US008115056B2

(12) United States Patent
Harrison et al.

(10) Patent No.: US 8,115,056 B2
(45) Date of Patent: Feb. 14, 2012

(54) ROOT-SPECIFIC PHOSPHATE TRANSPORTER PROMOTERS

(75) Inventors: Maria Harrison, Ardmore, OK (US); Zeng-Yu Wang, Ardmore, OK (US); Kai Xiao, Hebei Province (CN); Jinyuan Liu, Ardmore, OK (US)

(73) Assignee: The Samuel Roberts Noble Foundation Inc., Ardmore, OK (US)

( * ) Notice: Subject to any disclaimer, the term of this patent is extended or adjusted under 35 U.S.C. 154(b) by 421 days.

(21) Appl. No.: 12/257,271

(22) Filed: Oct. 23, 2008

(65) Prior Publication Data

US 2009/0113571 A1 Apr. 30, 2009

Related U.S. Application Data

(62) Division of application No. 11/400,771, filed on Apr. 7, 2006, now Pat. No. 7,534,932.

(60) Provisional application No. 60/669,242, filed on Apr. 7, 2005.

(51) Int. Cl.
C12N 15/82 (2006.01)
(52) U.S. Cl. ...................................................... 800/287
(58) Field of Classification Search ........................ None
See application file for complete search history.

(56) References Cited

U.S. PATENT DOCUMENTS

| 5,023,179 A | 6/1991 | Lam et al. ................... 435/172.3 |
| 5,097,025 A | 3/1992 | Benfey et al. .................... 536/27 |
| 6,376,746 B1 | 4/2002 | Kloti ............................ 800/278 |

FOREIGN PATENT DOCUMENTS

| JP | 2002-142766 | 5/2002 |
| WO | WO 98/38295 | 9/1998 |

OTHER PUBLICATIONS

EMBL Database Accession No. AC145767 submitted Jul. 25, 2003.*
GenBank Accession GI: 22082247 Feb. 10, 2003.*
Benfey et al., "The CaMV 35S enhancer contains at least two domains which can confer different developmental and tissue-specific expression patterns," *EMBO J.*, 8(8):2195-2202, 1989.
Brinch-Pedersen et al., "Engineering crop plants: getting a handle on phosphate," *Trends Plant Sci.*, 7(3):118-125, 2002.
Burleigh et al., "Functional diversity of abuscular mycorrhizas extends to the expression of plant genes involved in P nutrition," *J. Exp. Botany*, 53:1593-1601, 2002.
Chiou et al., "The spatial expression patterns of a phosphate transporter (MtPT1) from *Medicago truncatula* indicate a role in phosphate transport at the root/soil interface," *The Plant Journal*, 25:281-293, 2001.
Cho et al., "Regulation of root hair initiation and expansin gene expression in arabidopsis," *The Plant Cell*, 14:3237-3253, 2002.
Database EMBL, Database Accession No. AC145767, Jul. 25, 2003.
Database EMBL, Database Accession No. AC122171, May 30, 2002.

Database GenBank, Database Accession No. AC122161, Jul. 9, 2004.
Degenhardt et al., "A DNA binding activity for one of two closely defined phytochrome regulatory elements in an Lhcb promoter is more abundant in etiolated than in green plants," *The Plant Cell*, 8:31-41, 1996.
Dunn et al., "Identification of promoter elements in a low-temperature-responsive gene (blt4.9) from barley (*Hordeum vulgare* L.)," *Plant Mol. Biol.*, 38:551-564, 1998.
Engstrom et al. "Promoter bashing, microRNAs, and Knox genes. New insights, regulators, and targets-of regulation in the establishment of lateral organ polarity in arabidopsis," *Plant Physiol.*, 135:685-694, 2004.
Hammond et al., "Changes in gene expression in Arabidopsis shoots during phosphate starvation and the potential for developing smart plants," *Plant Physiol.*, 132:578-596, 2003.
Haran et al.,"Characterization of Arabidopsis acid phosphatase promoter and regulation of acid phosphatase expression," *Plant Physi.*, 124:615-626, 2000.
Hayes et al., "The growth and phosphorus utilisation of plants in sterile media when supplied with inositol hexaphosphate, glucose 1-phosphate or inorganic phosphate," *Plant and Soil*, 220:165-174, 2000.
Herr et al., "The SV40 enhancer is composed of multiple functional elements that can compensate for one another," *Cell*, 45(3):461-470, 1986.
Kim et al., "A 20 nucleotide upstream element is essential for the nopaline synthase (nos) promoter activity," *Plant Molecular Biology*, 24:105-117, 1994.
Liu et al., "Cloning and characterization of two phosphate transporters from Medicago truncatula roots: regulation in response to phosphate and to colonization by arbuscular mycorrhizal (AM) fungi," *Molecular Plant Microbe Interactions*, 11:14-22, 1998.
Liu et al., "Signaling of phosphorus deficiency-induced gene expression in white lupin requires sugar and phloem transport," *Plant J.*, 41:257-268, 2005.
Luscher, "New light on Myc and Myb. Part I. Myb.," *Genes Dev.*, 4:2235-2241, 1990.
Luscher, "New light on Myc and Myb. Part II. Myb.," *Genes Dev.*, 4:2025-2235, 1990.
Mudge et al., "Root-specific and phosphate-regulated expression of phytase under the control of a phosphate transporter promoter enables Arabidopsis to grow on phytate as a sole page source," *Plant Sci.*, 165:871-878, 2003. Mukatira et al., "Negative regulation of phosphate starvation-induced genes," *Plant Physiol*, 127:1854-1862, 2001.
Odell et al., "Identification of DNA sequences required for activity of the cauliflower mosaic virus 35S promoter," *Nature*, 313:810-812, 1985.
Piechulla et al., "Identification of tomato Lhc promoter regions necessary for circadian expression," *Plant Molecular Biology*, 38:655-662, 1998.
Potenza et al., "Invited review: targeting transgene expression in research, agricultural, and environmental applications: promoters used in plant transformation," *In Vitro Cellular and Developmental Biology Plant*, 40:1-22, 2004.
Rajewsky et al., "Computational detection of genomic cis-regulatory modules applied to body patterning in the early *drosophila* embryo," *BMC Bioinformatics*, 3:30, 2002.

(Continued)

*Primary Examiner* — Russell Kallis
(74) *Attorney, Agent, or Firm* — SNR Denton US LLP

(57) ABSTRACT

The current invention provides plant promoter sequences. Compositions comprising the promoter sequence are described, as are methods for the expression of transgenes in plants comprising the use of these sequences. The methods of the invention include the direct creation of transgenic plants with the promoters by genetic transformation, as well as by plant breeding methods.

22 Claims, 15 Drawing Sheets

OTHER PUBLICATIONS

Richardson et al., "Extracellular secretion of *Aspergillus* phytase from *Arabidopsis* roots enables plants to obtain phosphorus from phytate," *Plant J.*, 25:641-649, 2001.

Roe et al., "Sequencing gene rich regions of *Medicago truncatula*, a model legume," In *Molecular Breeding of Forage and Turf*, Hopkins et al., (Eds.), Kluwer Academic Publishers, Dordrecht, 333-344, 2004.

Rubio et al., "A conserved MYB transcription factor involved in phosphate starvation signaling both in vascular plants and in unicellular algae," *Genes and Development*, 15:2122-2133, 2001.

Schachtman et al., "Phosphorus Uptake by Plants: From Soil to Cell," *Plant Physiol.*, 116:447-453, 1998.

Schunmann et al., "Characterization of promoter expression patterns derived from Pht1 phosphate transporter genes of barley (*Hordeum vulgare* L)," *J. Exp. Botany*, 55:855-865, 2004.

Schunmann et al., "Promoter analysis of the barley Pht1;1 phosphate transporter gene identifies regions controlling root expression and responsiveness to phosphate deprivation," *Plant Physiology*, 136:4205-4214, 2004.

Smale et al., "The "initiator" as a transcription control element," *Cell*, 57(1):103-113, 1989.

Smale et al., "The RNA polymerase II core promoter," *Ann. Rev. of Biochem.*, 72:449-479, 2003.

Thum et al., "Analysis of barley chloroplast psbD light-responsive promoter elements in transplastomic tobacco," *Plant Mol. Biol.*, 47:353-366, 2001.

Urao et al., "An *Arabidopsis* myb homolog is induced by dehydration stress and its gene product binds to the conserved MYB recognition sequence," *The Plant Cell*, 5:1529-1539, 1993.

Vance et al., "Phosphorus acquisition and use: critical adaptations by plants for securing a nonrenewable resource," *New Phytol.*, 157:423-447, 2003.

Welsch et al., "Structural and functional characterization of the phytoene synthase promoter from *Arabidopsis thaliana*," *Planta*, 216:523-534, 2003.

Xiao et al., "Improved phosphorus acquisition and biomass production in *Arabidopsis* by transgenic expression of a purple acid phosphate gene from *M. truncatula*," *Plant Science*, 170:19-202, 2006.

Xiao et al., "Isolation and analysis of two root specific promoters from *Medicago truncatula*," *Third International Symposium on Molecular Breeding of Forage and Turf*, pp. 30, 2003.

Xiao et al., "Isolation and characterization of root-specific phosphate transporter promoters from *Medicago truncatula*,"*Plant Biol*, 8(4):439-449, 2006.

Xiao et al., "Transgenic expression of a novel *M. truncatula* phytase gene results in improved acquisition of organic phosphorus by *Arabidopsis*," *Planta*, 222:27-36, 2005.

Zhu et al., "TATA Box and initiator functions in the accurate transcription of a plant minimal promoter in vitro," *The Plant Cell*, 7:1681-1689, 1995.

Zimmermann et al., "Engineering the root-soil interface via targeted expression of a synthetic phytase gene in trichoblasts," *Plant Biotechnol. J.*, 1:353-360, 2003.

\* cited by examiner

```
F1533   TATTATATGCATGGGCTGGAGTTCGAATCCCGAACACCCCACTTCTCCACATTTAAAAATGTGAACTCAAGTCACTATG   -1470
        TTATTTGACCAAAAAACAAAATGAGAAAAAAAGACCAAGCGGGAAAAGTACCCATTTACCAAGTCGATACAAATAC     -1390
        TAATTGACTTTTTATTTTGTTAAAAATAATAATTGACTTTTTTTAGGGGAAATAATAATTGACATTTTTTTTA        -1310
        ATATTTTTGACAAAAAATTGACTTTATGTACCGATTATAATTCATAAACCCACATAATATATAACGTCATAGTTTAATTG -1230
        ACAGTTGGTCTGAAACAAAATATAGTTTAACTTGTTTAGTTTTTTAGAGGAGTAAATGCCAGTTGGTTGCATTGCATA   -1150
        ATATGGCGCATGCACGAGTTGATATATACTATTTGATTTGAATAAGATATACGATACTTGTACGTTTTGTACTTGTGATA -1070
        TATTATGTTATTGCGGAATATTTTATGAAAAAATTTATGGTTGACATTCAAACTAAAATGTTTACTTAATGGTAGAGTTA -990
D975    TAAACCTCGGCTCCGCGTAAGCACATAGCTCAGTTGGCAGAGACATGCATTATTATATGTAGGGGCTGGGGTTCAAACCCCG -910
        GACACCCCACTTATTCATCTTGAAAAATATGAATTCTAACCACTAAATTACTTGACCAAAATAACCCAAAATCCTGATGT -830
        AGGAGATCCTCTGATTAATATATTGAGCATATCCTCAAGTGGAATCAATGTCAAATATCGTTAATTCCTAACGATGTC   -750
        GGTATTAAATATATTGTTCATTGTTATGTCTATGTATTAAGAATGAATAATTACTTAAAAAACTATAAAATTAATAATGG -670
        CTATATTTTTCATTGGTTACAAAAAATAGTGCTTGTGAAGCGTTGACATTGGTGAATGCTTATGATTAATTAGGCATATACCCCAT -590
        TTTTATTAAGTTACAAAATTGATTCTTTTGACTTTTGACATTCCTGATTTGGCTAGGATTGTTACCTATATAGCTGAGTTGA -510
        TGATGCTAAATTGATTCTTTTGACTTTGACATTCCTGATTTGGCTAGGATTGTTACCTATATAGCTGAGTTGA -430
D551    TTATCTGCTCACAGTGTGCATAAACCTAGTCTTCATACCACTTTACTTCTTCTTATCAACTTGGCTTTTTTCTTGCAAGAGTAC -350
D342    GAACTCTATCTATCTCCCTTATTGAGTTTGTAGACACCAAATGAGTATTCATGTTGTACATTTTTTTTGGCAAATCTTG -270
        GTCGCATCATACAACTGTAGAGATTAAATGGCTCGAGATAACTAAGATATATTTAAAGAGTTTAGTACTCGAGTGTATGTG -190
D133    TGTATAAAAATATATATAATTTTCATTGGTATTAGGCACAATTTAGGTAGGTTACTTTATAGTTTTGAGCAGTTTATCCA -110
        TTTCTTACCTCAGCCTCACAAATGTCAAGTTAGTTTTTTTTGTTTACTAATATTTAATGTGTCTTGTCTTAATTATG    -30
Rev     CAGGGAAAAACTAGGTAACAAATTCAGTCATGTCTGGAGAATTAGGAGTGCTTAATGCACTCGATGTCGCAAAGACGCAA   51
```

FIG. 1

```
F'1238  TTATTGAATTAGAGGCCACTTGTCTTTATTTTTAAGGGCAGGGACCACCTTGTTATTGCTTAAAATTGAACGAAAATA  -2348
        TTAAGATTATAGTCTCTTTAGATTACTTAAAAATCAACAAGCAAACTATGAATTTATGATATAGCATAATA        -2268
        GAAACTATTATACAAACCCAGAATTTGTGTAATTGGAGAACCTCTAACTACCAGTATAGTGAATAATTGGGTTGCAACAGA -2188
        TACAAGGGGTATTAAATATATTGAGCATATATCTGTTTCCACAAGTGAATCAATCTAAAATATCTCTTAA        -2108
D'962   TTACCTTAAGTGAATGGATGTCCTAGATTTTAATTGGTTATGTATCTGTATTAAGGATATATTACTCGGAAAGAATAA -2028
        ATTAGCATGTGAACTATTATAGTTCCTACAGATGTTTAAAAAAGTCAACTATTATATGGTTTTCCTAAAAAAGAGTAAAT -1948
        TACACTTCGCTTTCCTTTCCTACAGATGTTTCCATCTCCTCTTATATTAAAATATACATTTTATTCTCCTCTT    -1868
        ATTCAAAACATATTATGCTAAAAAAAAAATCTATTAGGATTTTGAACATGTTGAACAACATAATTGTTTACTTAAGTCT -1788
D'586   TAAGGTGTGTTAAATCTCCTTTAGGTCAACATCCCGAAATTTATGCTTAAGCATGTTTAAATTTGTGATTAATGAAATTACTT -1708
        TGGTGATTAGCTAGTGAATTCAACTCTTGATATATCCAATAGCAATTGCCGCAAAAGTGTATAAAGTTGTACAA    -1628
        ATATCATTTATCTATAATACATTTTTCATTCCTAATTTTATACAATGATGTGTTTCTGTTAATGTTAAGTGTAATGCTTCAAGTT -1548
        TTTCCTATATTATTACATTTTAATTACATAACTAGCATTCAGATTTAAGAAACAAGAAAAATTAATTAAAAAAATAGTGCTTATAAAGCG -1468
D'266   TAATCATTAATTAACATAACTAGCATTCAGATTTAAGAAACAAGAAAAATTAATTAAAAAAATAGTGCTTATAAAGCG -1388
        TTTACATTGATGAATGCTTGTGTAGTTAGGTGATTAGGTTAGGCATATACCATTGATGCTGAATTGATTCCTTTGACCTAGCA -1308
D'126   AGGTTCATGTTACCTATATATGCATATATTAATAGTTTAGCTGCTCAAAGTGCAGGCACCTAGCTAGGTAA     -1228
Rev     CTTGACTTCTCACAAGGAGGTCTTCTCTCTATCTCTCTCTAGCTTGGGACTAGGTAA.........CAAATTCAGCCATGTC  +5
                                                                        intron
```

FIG. 2

```
GTGATCTGCAGGTGCAGCTTGACAACCGACTAGGTTAGAATATCACATTGACCTTATCACTTATATAGTGTACCTAAGATAAATA
AATGCGACATTACTGTTACTTAATATCCAACAATATAAACAGGGTGATTCGAATCCTAACCGCTGCTTACTTTTCTGCAACCAA
AAATAGGTAAACTTGCTCTCTGTTGCAATCAGATAGATAAAAATTGCAAGACATCTAACCCTTATATATTTATATCGTCAACTTACAAAAAT
AAGTAACAAGAATTGTTTGGACGAAACGACTTTCCTTTTGGATACGATACTCTACTTATCAGTTTATTACTTGTTAAACGATTTG
GTACACTGGCGACATTCGACCATCGACCATCATAGAGCTCTAGCCGTCGACACGATTATGAGTTAGCCTCAATCTGGTTTTGCTATGTTTG
TTAGTTTCTGTTTATTTGCATTTGTTTTTATTTGTTCAGTGGAAGATGGAAGATGGGTGGTGGCTTTGTTTCGGCTATGTGATTTG
GTATGAAAATCTTGAATCTGATTTTCTGAATTAATGATATGGTTCTTTATTTAGGGTGTGTTCTGTTGGATGCATATCTCGAT
TCAACATGACTGCTTTTATCCTAAGTTGCTTGAAAGGTTAGTTGCGTAGATGCCCCGTGTGATGGTAGTGTCGTTCATCGT
ACCTAAAGTATTTATCCACCGTGGTTTCTTTTTGTATCATTGGTGGACAATGATATTTATATTGTTGTTCATCACTCGATG
TGCCGATGAAATTCAAGATCACTACGACTCTGTGAATTCATTTGCGTTTTTTTTGCAATTCCGTTTCGCCCACATATGTAGGTTCGCCA
GACCAATACATCTATTTAAATGCTTAGAATATTCATTTTGCGTTTTTCATTTTGTTATTACCACTTTTGTACCGACTTTATTTACGGATTAATTATCATC
GATTTCCATGCTAGTGGTTGTCTAGAGTTAGTTCTCTCTTTTGATTGTCATCATAGTTTGATTGTCATATATTATGTTGATATACTATTTGACGAGTG
ATAAACCCACATAATATAATGTCATAGTTTGATTGTCATATATTATGTGTAATAGTTTATGGTTGACATTCCAACTA
TTTGGTTGGTACGTTTGTACGTTTGTAGAGTTATACAAATCTGATGTCGGAGATCCTCAAATTAATGTACATATAGTTGAATATT
AAAAATTTACTTAAGTGTAGAGGGTATTAAATATTGAGCATATCCTCAAGTGAATCAATGTCAAATCTGAAATATCGTTAATT
AGGTTGCAACAGATACAAGGGATGTCCTAGATTTTAATTGTCATGTCTATGTATTAAGTATATATATTACTTAAAAGTATAAATTAATT
TCCCTAAGTAGAATAAGGGTGCAAAACTGCAAATTTAAACAAAAATAGTGCTTGTGAAGGGTTGACATTGATGAATGTTTATGATTAAT
AGAGCCCGTTGCTGCTAGAAACTGCAAATTTAAACAAAAATAGTGCTTGTGAAGGGTTGACATTGATGAATGTTTATGATTAAT
GAGGCATATACCCCATTGATGCTAAATTGATTCTTTTTAACTCATGAGGCATACCTGGCTTGGCTTGCCACTTTACTTCTTATCCACTTTACTTCTTTATCAACTTGGTTTCTTGCA
TAGCTGAGTTTAATTATCTGCTCACAGTGTGCATAAACCTAACTCCTTATACCACTTTACTTCTTTATCAACTTGGTTTCTTGCA
AGGAG
```

FIG. 3

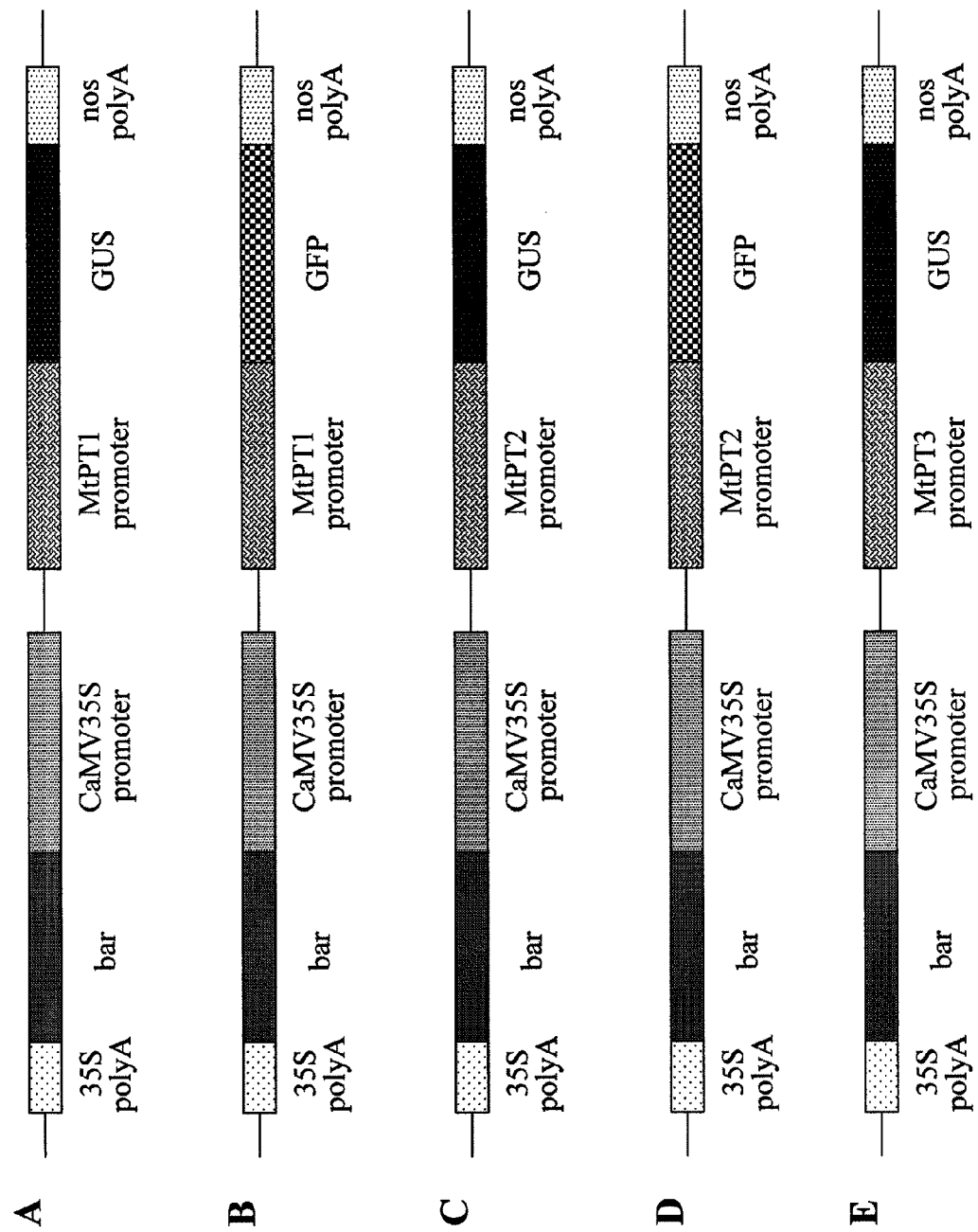
FIG. 4A-E

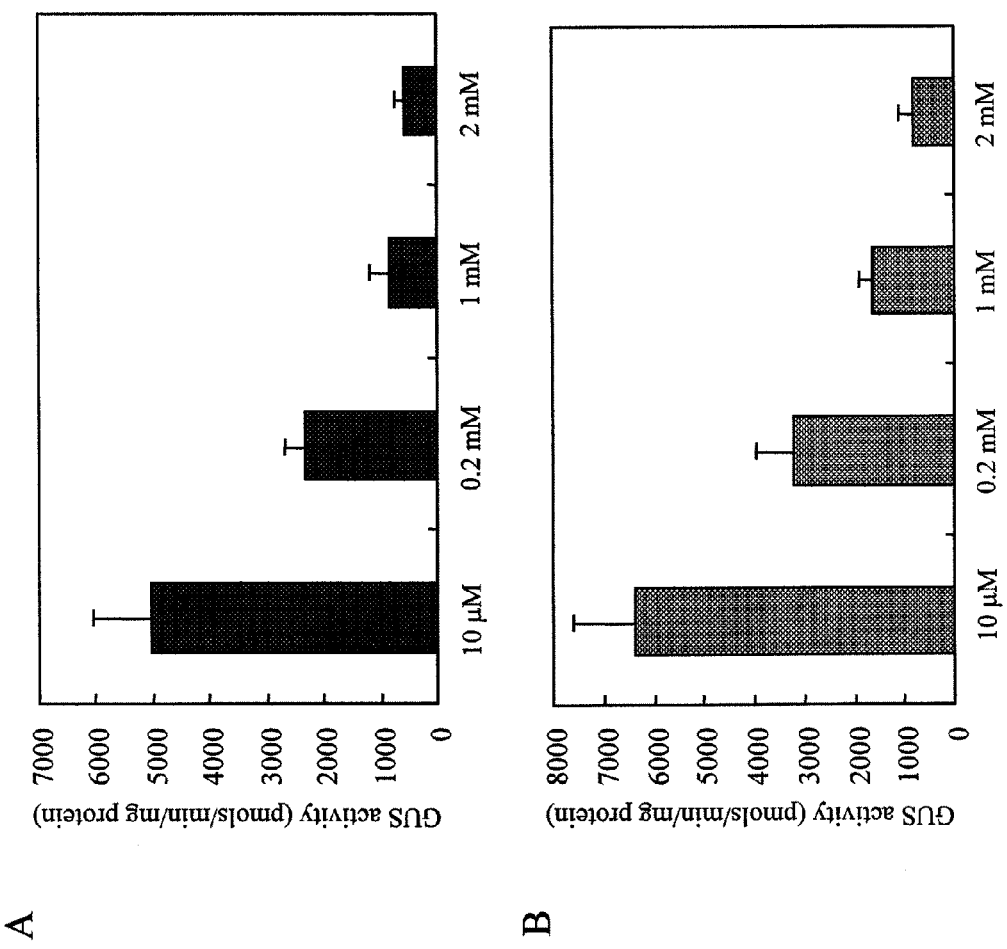
FIG. 8A-B

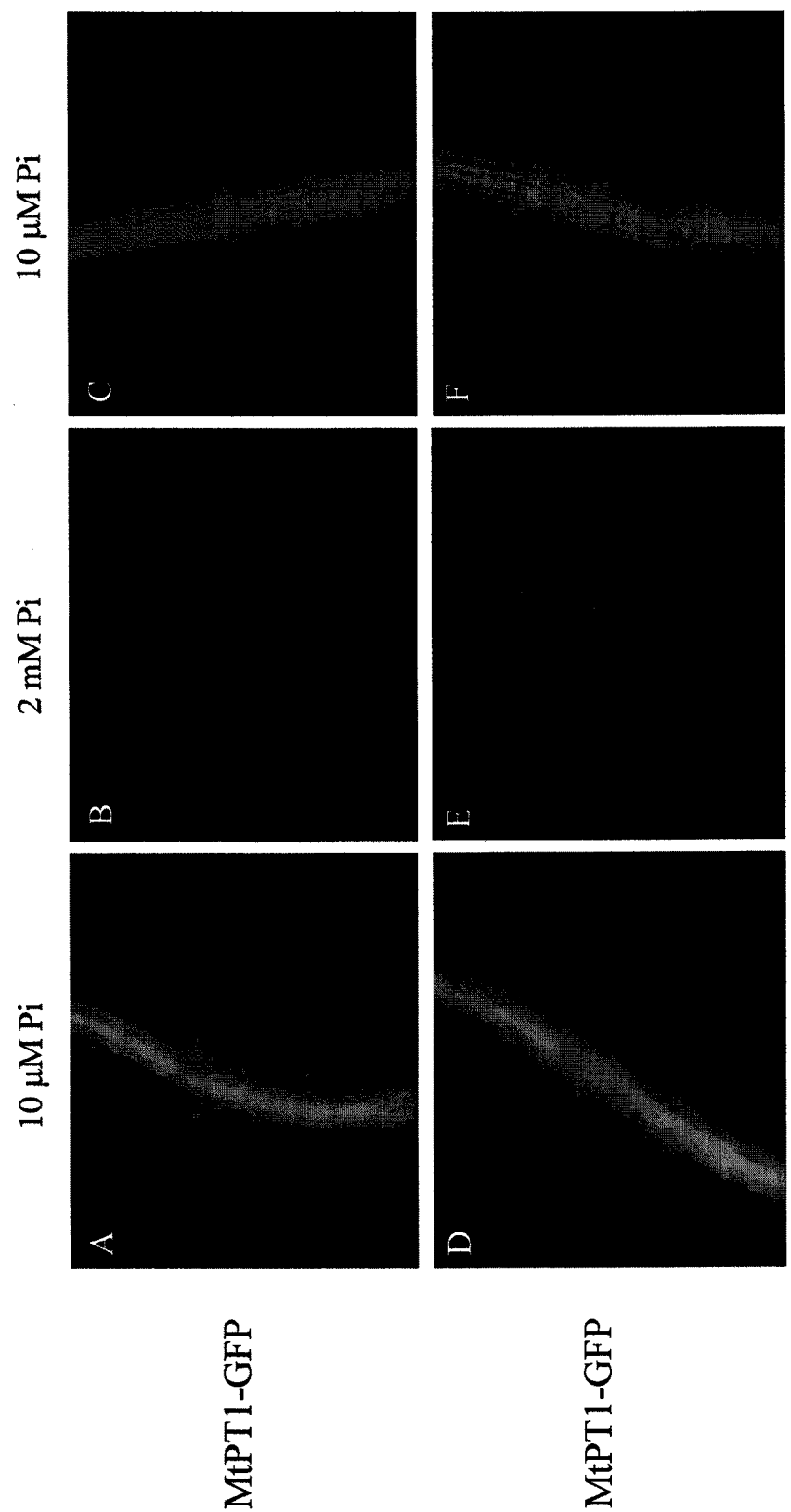
FIG. 9A-F

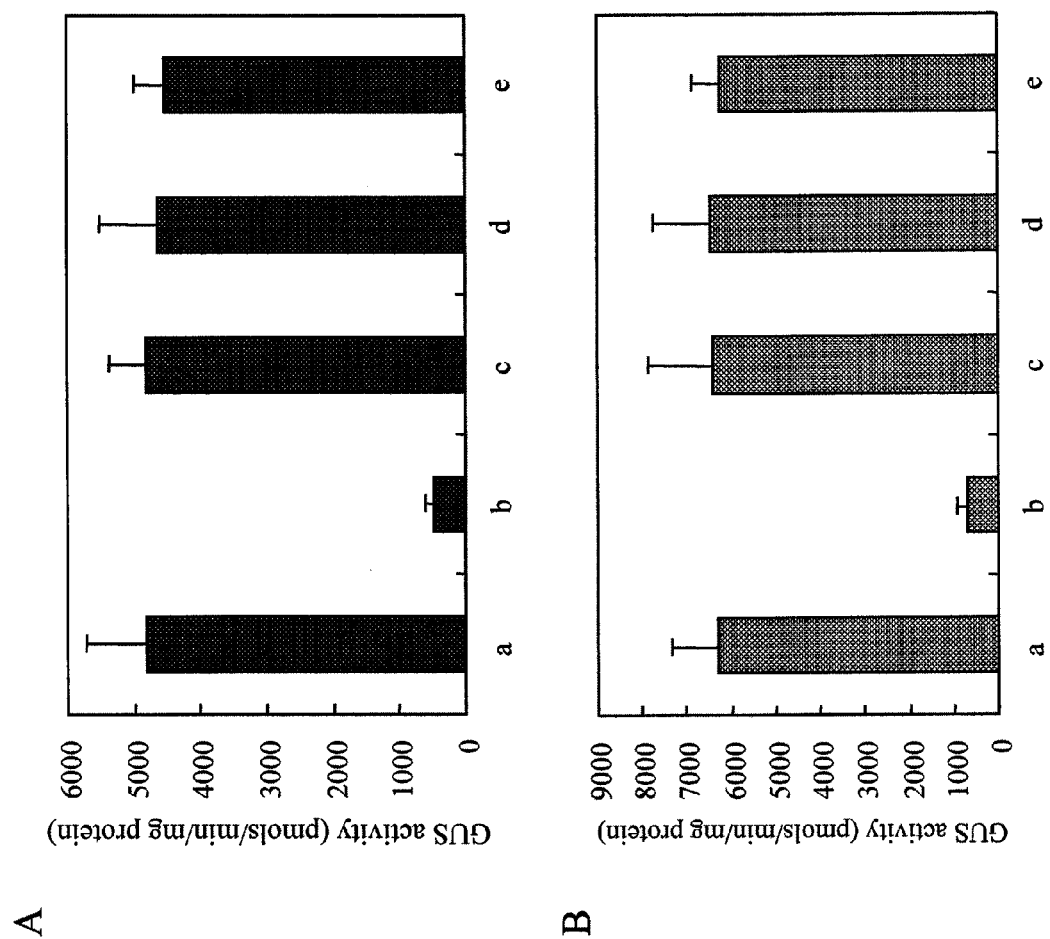
FIG. 10A-B

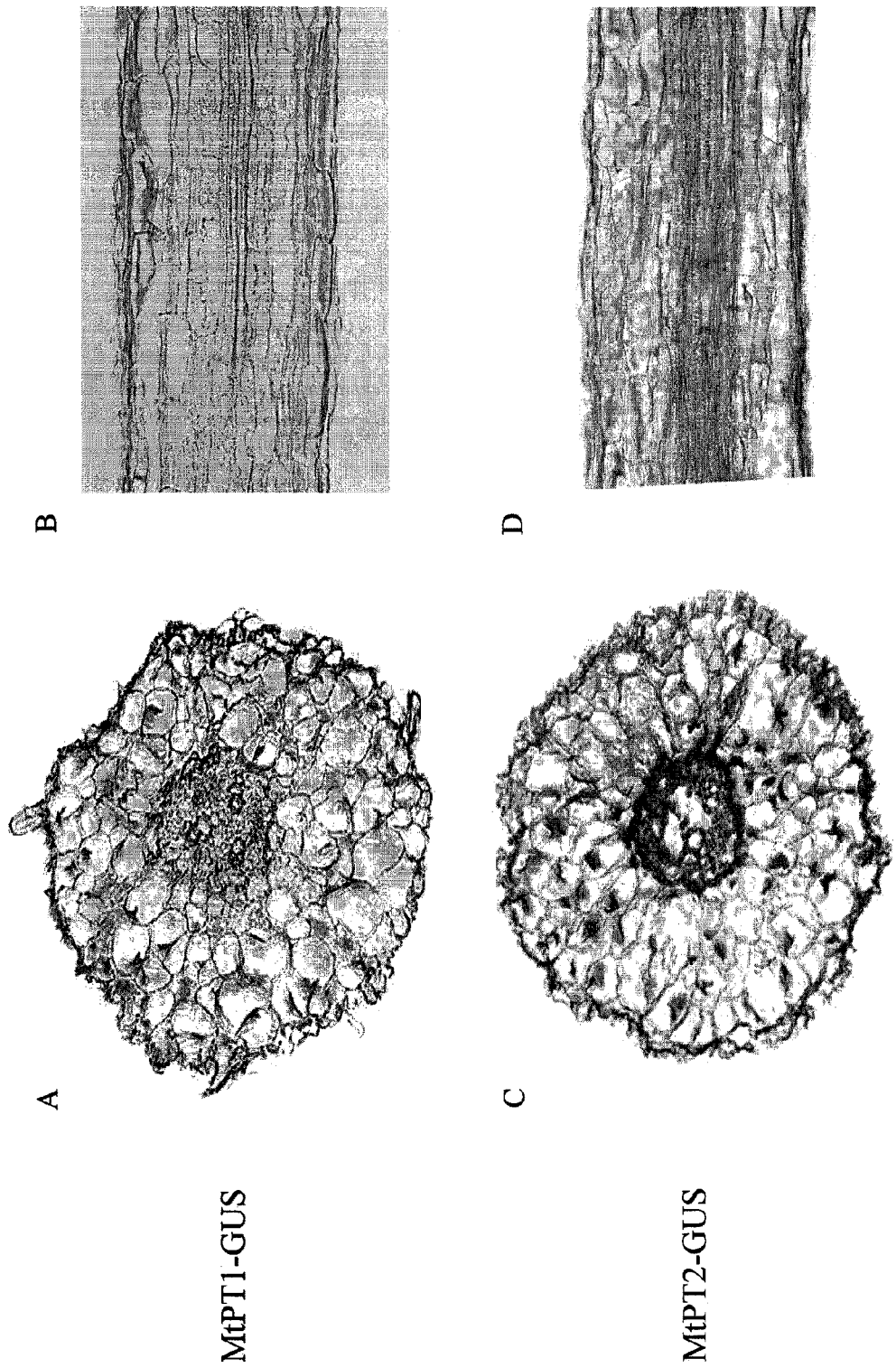
FIG. 11A-D

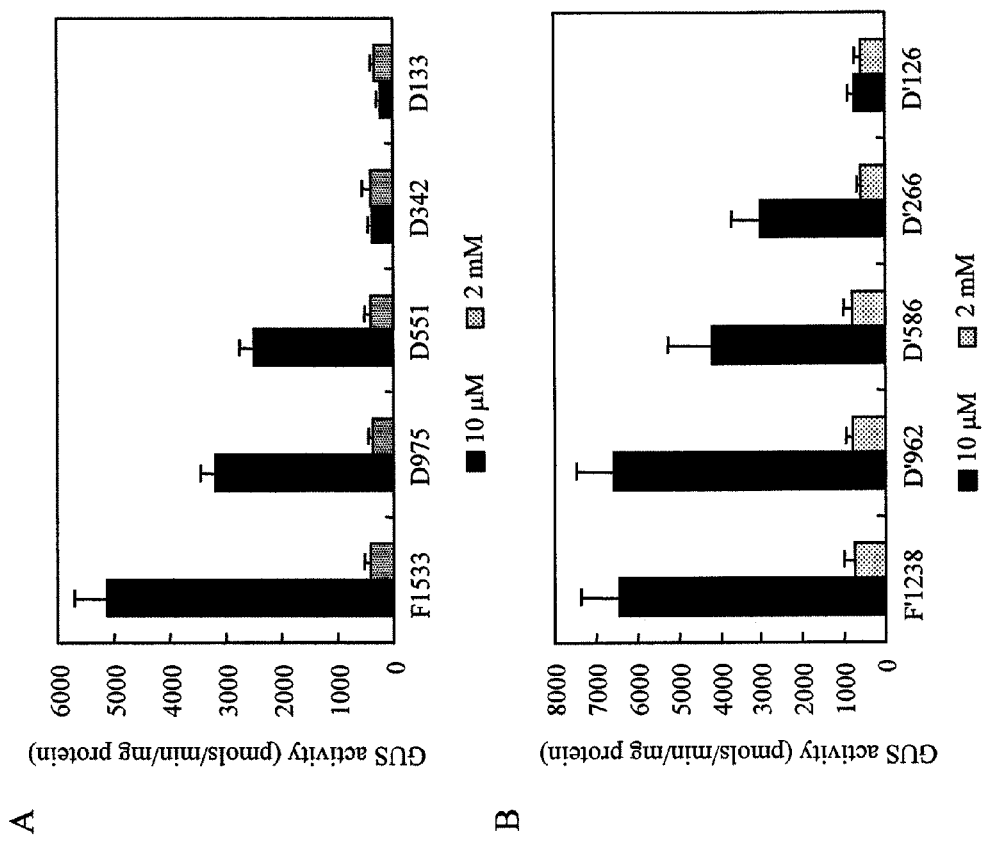
FIG. 12A-B

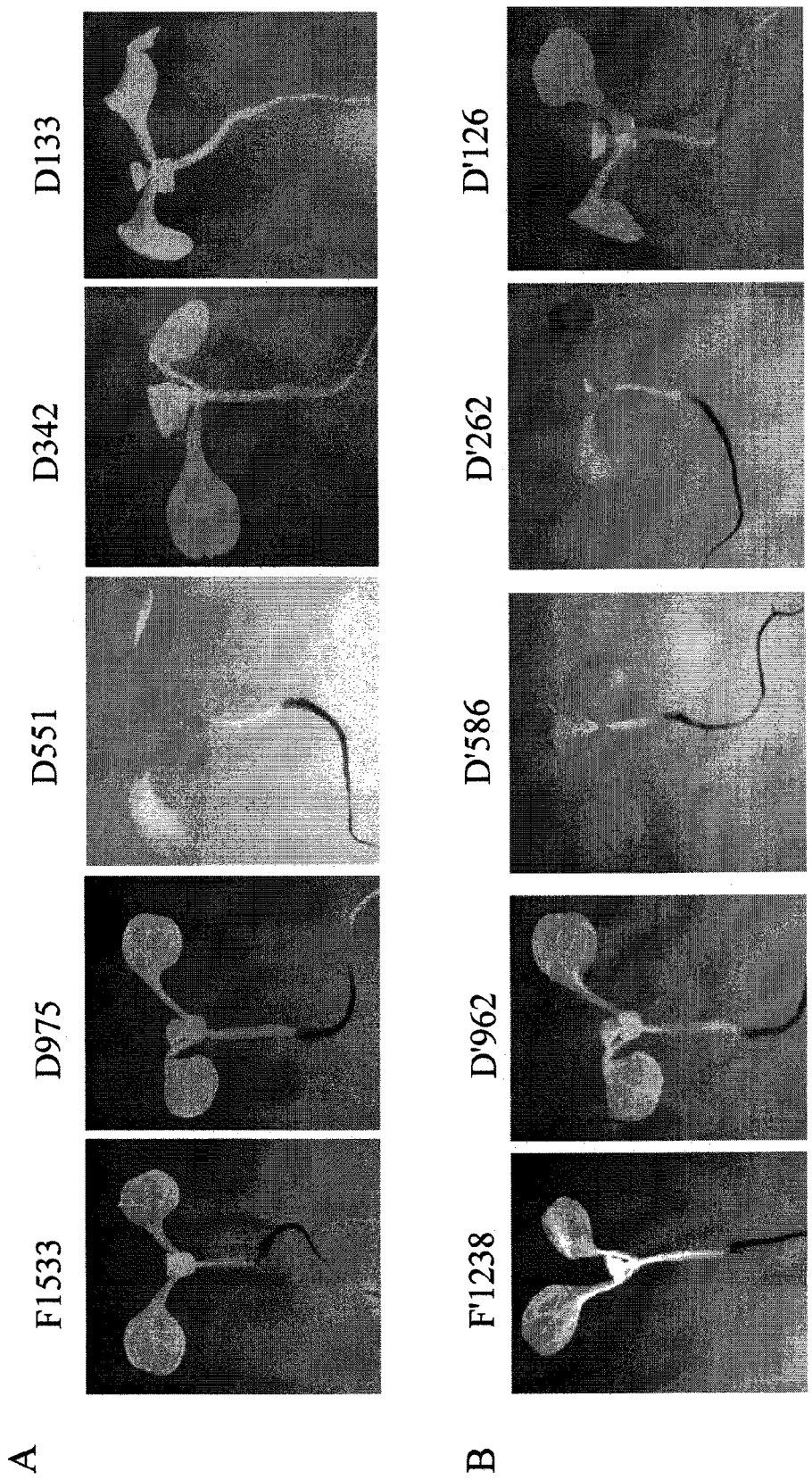
FIG. 13A-B

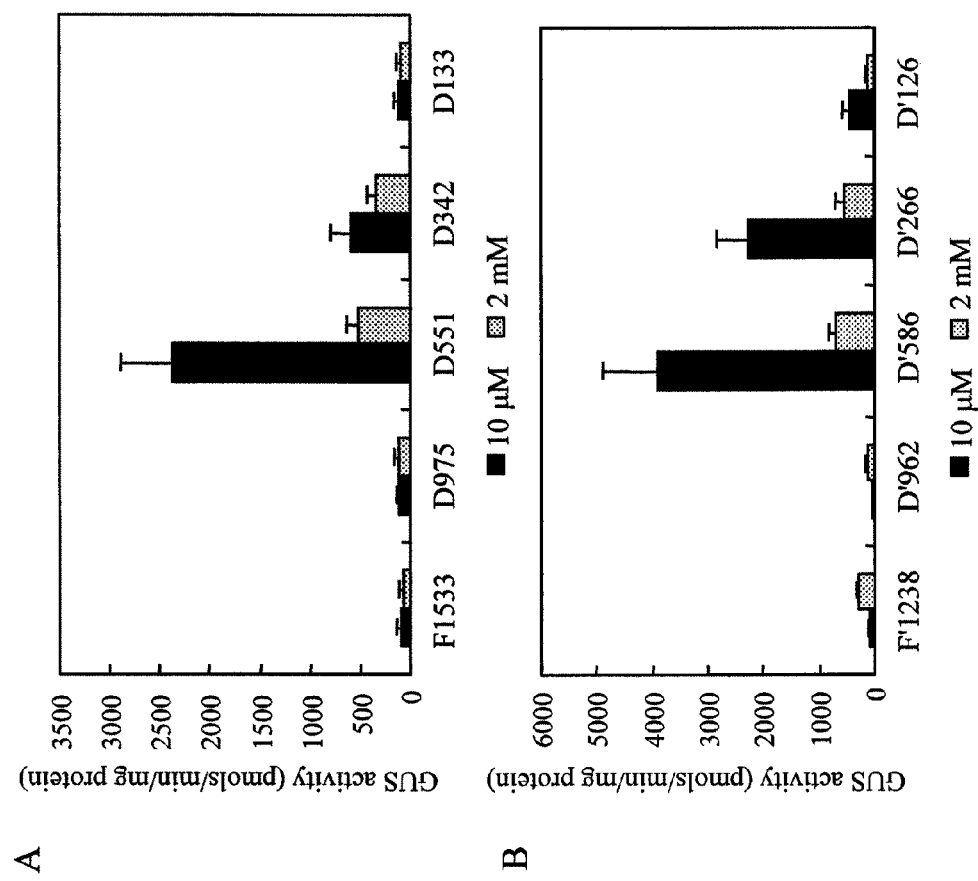
FIG. 14A-B

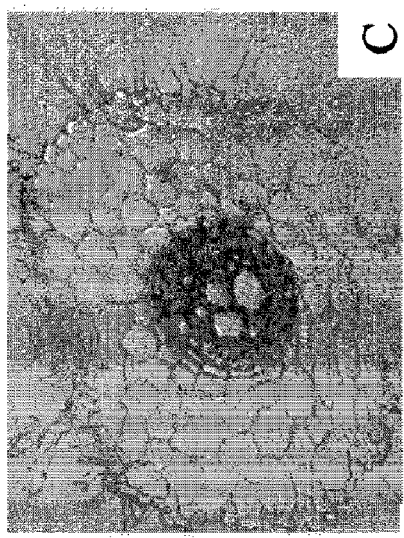
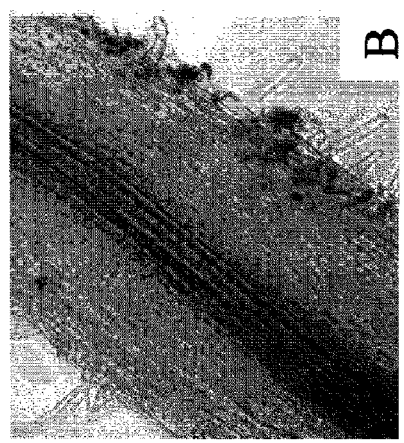
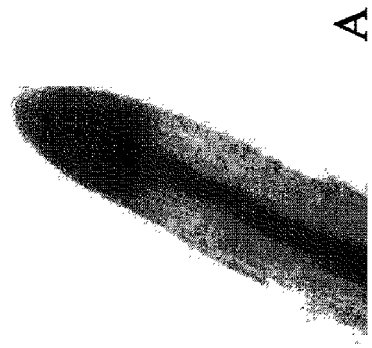
FIG. 15A-C

US 8,115,056 B2

ROOT-SPECIFIC PHOSPHATE TRANSPORTER PROMOTERS

This application is a division of U.S. application Ser. No. 11/400,771, filed Apr. 7, 2006, now U.S. Pat. No. 7,534,932, which claims the priority of U.S. Provisional Appl. Ser. No. 60/669,242 filed Apr. 7, 2005, the entire disclosures of which are incorporated herein by reference.

BACKGROUND OF THE INVENTION

I. Field of the Invention

The present invention generally relates to new regulatory sequences with defined tissue specificity. More specifically, the invention relates to the discovery of gene promoters for tissue specific and inducible expression of transgenes for the improvement of plant species.

II. Description of Related Art

Molecular improvement of crops presents both new challenges and clear opportunities for the application of biotechnology. Genetic modification of traits should enhance economics, human and animal health, and the environment. Such modifications require the efficient expression of transgenes with appropriate expression patterns. Regulatory elements with the appropriate expression profile are thus needed.

Most previous studies have used available strong constitutive promoters, such as the cauliflower mosaic virus 35S (CaMV35S) promoter. However, some constitutive promoters do not work in certain plants and typically do not provide tissue-specific or inducible expression in most environments. There has been a general lack of appropriate regulatory elements for inducible and tissue-specific expression in particular.

The ability to express transgenes in an inducible and/or tissue-specific manner is significant because it allows targeted expression to relevant plant tissue(s) under conditions in which transgene expression will benefit the plant. Expression of transgenes in plant tissues in which expression would not benefit the plant may have a deleterious effect on the plant or decrease available energy for expression of other proteins in the relevant tissues, depending upon the transgene expressed. Government regulatory issues may also be simplified by limiting gene expression primarily to inedible plant portions.

One plant characteristic for which genetic modification could greatly benefit the environment and farmers alike is increased phosphorous utilization from soil. Phosphorus is a major mineral nutrient that frequently limits crop production. The form of phosphorus most readily accessed by plants is phosphate (Pi), which is relatively immobile in the soil and often unavailable for plant uptake (Schachtman et al., 1998). Pi levels in soil are occasionally as high as 10 µM, but more frequently as low as 1 µM. In contrast, Pi concentration in plant cells is much higher, in the 2-20 mM range (Vance et al., 2003).

The identification of strong phosphate deficit-inducible promoters in particular could provide a significant advance in the art by allowing improvements for phosphate utilization under only appropriate conditions. Natural phosphorous sources are subject to depletion, while low levels of phosphorous can significantly deplete agricultural productivity and applications of phosphorous-rich fertilizers create run off polluting water sources. The identification of unique regulatory elements capable of use for engineering phosphorous uptake or other traits would therefore represent a significant benefit to agriculture and the environment alike.

SUMMARY OF THE INVENTION

In one aspect, the invention provides an isolated nucleic acid sequence comprising a promoter sequence operable in a plant, wherein the promoter comprises a nucleic acid sequence selected from the group consisting of SEQ ID NO:1 SEQ ID NO:2, and SEQ ID NO:3; or a fragment thereof having promoter activity. In certain embodiments, the fragment may be further defined as comprising at least 25, 50, 75, 95, 125, 250, 500 or more contiguous nucleotides of SEQ ID NO:1 or SEQ ID NO:2 or SEQ ID NO:3, up to and including the full length sequence. The isolated nucleic acid sequence may further be defined as operably linked to any desired elements, including an enhancer and/or coding sequence.

In yet another aspect, the invention provides a transformation construct comprising: (a) an isolated nucleic acid sequence comprising a promoter sequence operable in a plant, wherein the promoter comprises a nucleic acid sequence selected from SEQ ID NO:1, SEQ ID NO:2, and SEQ ID NO:3; or a fragment thereof having promoter activity; and (b) a heterologous coding sequence operably linked to said promoter sequence. The coding sequence may, in certain embodiments, be operably linked to a terminator, an enhancer and/or a selectable marker. The transformation construct may further comprise at least a second promoter. The transformation construct may also comprise a screenable marker.

In still yet another aspect, a plant is provided that is transformed with a selected DNA comprising a promoter sequence described herein. The plant may be further defined as a dicotyledonous or monocotyledonous plant. The invention further provides a cell and seed of such a plant. In still yet another embodiment, a progeny plant of any generation of a plant of the invention is provided, wherein the progeny plant comprises a selected DNA in accordance with the invention.

In certain other embodiments of the invention, nucleic acids hybridizing to SEQ ID NO:1 or SEQ ID NO:2 or SEQ ID NO:3 under stringent conditions and having promoter activity are provided. Stringent conditions may be defined as 5×SSC, 50% formamide and 42° C. By conducting a wash under such conditions, for example, for 10 minutes, those sequences not hybridizing to a particular target sequence under these conditions can be removed. Provided in still further embodiments of the invention are sequences having at least 90% sequence identity to a nucleic acid sequence selected from SEQ ID NO:1, SEQ ID NO:2, and SEQ ID NO:3 and fragments thereof having promoter activity, including at least about 92%, 95%, 98% and 99% homology to these sequences. Specific examples of such fragments of SEQ ID NO:1 and SEQ ID NO:2 include SEQ ID NOs:20-29. Exemplary fragments of SEQ ID NO:3 include last 1,000 or 500 or 300 nucleotides of the sequence.

In still yet another aspect, the invention provides a method of expressing a polypeptide in a plant cell comprising the steps of: (a) obtaining a construct comprising a promoter sequence of the invention operably linked to a heterologous coding sequence encoding a polypeptide; and (b) transforming a recipient plant cell with the construct, wherein said recipient plant cell expresses said polypeptide. In the method, the plant cell may be further defined as a dicotyledonous or monocotyledonous plant cell.

In still yet another aspect, a method of producing a plant transformed with a selected DNA comprising a promoter of the invention, comprising: (a) obtaining a first plant comprising the selected DNA; (b) crossing the first plant to a second plant lacking said selected DNA; and (c) obtaining at least a first progeny plant resulting from said crossing, wherein said progeny plant has inherited said selected DNA. In the method, the plant may be further defined as a dicotyledonous plant or monocotyledonous plant.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein:

FIG. 1. Promoter sequences of MtPT1 (SEQ ID NO:1). Deleted promoter segments are shown by arrows.

FIG. 2. Promoter sequences of MtPT2 (SEQ ID NO:2). Deleted promoter segments are shown by arrows.

FIG. 3. Promoter sequences of MtPT3 (SEQ ID NO:3).

FIG. 4A-E. Schematic illustrations of the MtPT1-GUS (FIG. 4A), MtPT1-GFP (FIG. 4B), MtPT2-GUS (FIG. 4C), MtPT2-GUS (FIG. 4D), MtPT3-GUS (FIG. 4E) binary vectors used for Agrobacterium-mediated transformation.

FIG. 8A-B. GUS activity of transgenic Arabidopsis roots carrying gene construct of MtPT1-GUS (FIG. 8A) and MtPT2-GUS (FIG. 8B) under different Pi concentrations. The Pi concentrations in the growth media were 10 µM, 0.2 mM, 1 mM and 2 mM, respectively. Error bars represent standard error.

FIG. 9A-F. Reversibility of GFP expression in transgenic Arabidopsis roots carrying gene constructs MtPT1-GFP and MtPT2-GFP. (FIG. 9A, D) Transgenic Arabidopsis growing at 10 µM Pi for 14 days. (FIG. 9B, E) 14-day-old plants were transferred to 2 mM Pi conditions for 2 days. (FIG. 9C, F) Transgenic plants were transferred back to 10 µM Pi conditions for 2 days.

FIG. 10A-B. Reversibility of GUS expression in transgenic Arabidopsis roots carrying gene constructs of MtPT1-GUS (FIG. 10A) and MtPT2-GUS (FIG. 10B). Transgenic Arabidopsis were grown at 10 µM Pi for 14 days (a), transferred to 2 mM Pi conditions for 2 days (b), then transferred back 10 µM Pi for 2 days (c), 7 days (d) and 15 days (e). Error bars represent standard error.

FIG. 11A-D. Sections of M. truncatula transgenic roots carrying gene constructs MtPT1-GUS (FIG. 11A, B) and MtPT2-GUS (FIG. 11C, D).

FIG. 12A-B. GUS activity of transgenic Arabidopsis roots carrying deleted MtPT1-GUS gene constructs (FIG. 12A) and MtPT2-GUS gene constructs (FIG. 12B) with varying lengths of promoter region under Pi concentrations of 10 µM Pi and 2 mM. Error bars represent standard error.

FIG. 13A-B. GUS staining of transgenic Arabidopsis carrying deleted MtPT1-GUS gene constructs (FIG. 13A) and MtPT2-GUS gene constructs (FIG. 13B) with varying lengths of promoter region.

FIG. 14A-B. GUS activity of transgenic Arabidopsis leaves carrying deleted MtPT1-GUS gene constructs (FIG. 14A) and MtPT2-GUS gene constructs (FIG. 14B) with varying lengths of promoter region under Pi concentrations of 10 µM Pi and 2 mM. Error bars represent standard error.

FIG. 15A-C. GUS staining of M. truncatula roots expressing the MtPT3-GUS gene construct. GUS expression in whole roots (FIG. 15A and FIG. 15B) and in cross-sections of the root (FIG. 15C). As shown in each panel, GUS staining indicates that the MtPT3 promoter drives expression in the vascular tissues.

DETAILED DESCRIPTION OF THE INVENTION

Figure 5:
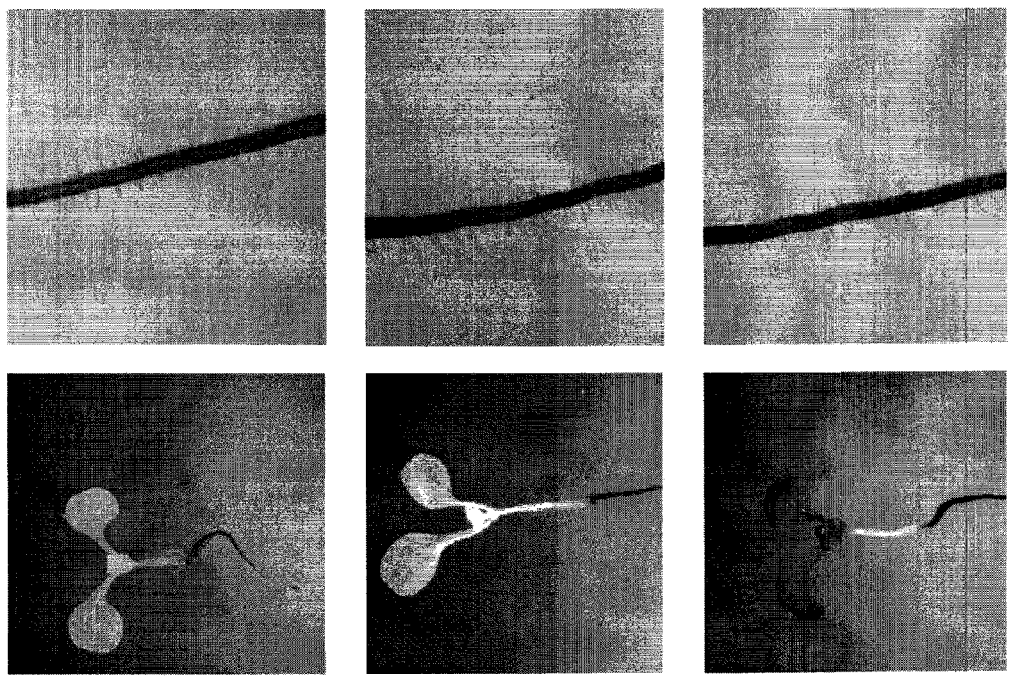
FIG. 5. GUS staining of transgenic Arabidopsis carrying MtPT1-GUS, MtPT2-GUS and CaMV35S-GUS gene constructs, respectively. The Pi concentration in the growth medium was 10 µM.

The invention overcomes the limitations of the prior art by providing promoters with unique and inducible expression profiles. Transgenic expression of three promoters, designated MtPT1, MtPT2 and MtPT3 revealed root-specific and inducible expression sensitive to phosphate (Pi) deficit. The promoters lead to different patterns inside root tissues. Promoter deletion analysis revealed sequences involved in Pi deficit responsiveness. The promoters are of particular value for defined engineering of plants, in which root-specific expression of transgenes, as well as inducible expression, may be preferred or required.

One aspect of the current invention comprises the MtPT1, MtPT2 an MtPT3 promoter sequences, exemplified by SEQ ID NO:1, SEQ ID NO:2, SEQ ID NO:3 and fragments thereof having promoter activity. In certain embodiments of the invention, such a fragment may be a restriction fragment, for example, from a complete or partial digest by one or more restriction enzymes including, but not limited to, HaeIII, PaeI, ThaI, TruII, TaqI, BfaI, AccII, AluI, CfoI.5, EcoRI BamHI. Fragments may also routinely be made by mechanical shearing of DNA as well as use of non-specific nucleases. Exemplary fragments comprise, in one embodiment, at least about 60, 80, 100, 150, 200, 300, 500, or 800 or more contiguous nucleotides of the sequence of SEQ ID NO:1 or SEQ ID NO:2 or SEQ ID NO:3 up to the full length sequence. The screening of promoter sequences for activity is routine in art and can efficiently be carried out by the methodology described in the working examples. In this manner, large number of promoter fragments may be linked to screenable markers and transformed into plant cells ex vivo for transient assays of marker gene product. Using visual detection, for example, promoter activity is readily identified.

Also provided by the invention are sequences substantially identical to a promoter sequence provided herein. "Substantially identical" refers to a nucleic acid sequence exhibiting in order of increasing preference at least 90%, 95%, 98 or 99% identity to a promoter nucleic acid sequence provided by the invention, for example, SEQ ID NO:1 and/or SEQ ID NO:2 and/or SEQ ID NO:3 and fragments thereof having promoter activity. Polynucleotide comparisons may be carried out using sequence analysis software, for example, the Sequence Analysis software package of the GCG Wisconsin Package (Accelrys, San Diego, Calif.), MEGAlign (DNAStar, Inc., 1228 S. Park St., Madison, Wis. 53715), and MacVector (Oxford Molecular Group, 2105 S. Bascom Avenue, Suite 200, Campbell, Calif. 95008). Such software matches similar sequences by assigning degrees of similarity or identity. Such comparisons may be made using default parameters.

Techniques for engineering promoter sequences at the nucleotide level are also known, for example, using site-directed mutagenesis, and may be used to produce promoter derivatives. This is typically performed by first obtaining a single-stranded vector or melting apart of two strands of a double-stranded vector which includes a DNA sequence which comprises a promoter of the invention. An oligonucleotide primer bearing the desired mutated sequence is prepared, generally synthetically. This primer is then annealed with the single-stranded vector, and subjected to DNA polymerizing enzymes such as the E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as E. coli cells, and cells are selected which include recombinant vectors bearing the mutated sequence arrangement. Vector DNA can then be isolated from these cells and used for transformation.

A genetic selection scheme was devised by Kunkel et al. (1987) to enrich for clones incorporating mutagenic oligonucleotides. Alternatively, the use of PCR with commercially available thermostable enzymes such as Taq polymerase may be used to incorporate a mutagenic oligonucleotide primer into an amplified DNA fragment that can then be cloned into an appropriate cloning or expression vector. The PCR-mediated mutagenesis procedures of Tomic et al (1990) and Upender et al (1995) provide two examples of such protocols. A PCR employing a thermostable ligase in addition to a thermostable polymerase also may be used to incorporate a phosphorylated mutagenic oligonucleotide into an amplified DNA fragment that may then be cloned into an appropriate cloning or expression vector.

The term "template-dependent process" refers to nucleic acid synthesis of a RNA or DNA molecule wherein the sequence of the newly synthesized strand of nucleic acid is dictated by the well-known rules of complementary base pairing. Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety. A number of template dependent processes are available to amplify the target sequences of interest present in a sample, such methods being well known in the art and specifically disclosed herein below.

An efficient, targeted means for preparing promoters relies upon the identification of putative regulatory elements within the target sequence. This can be initiated by comparison with, for example, promoter sequences known to be expressed in a similar manner. Sequences which are shared among elements with similar functions or expression patterns are likely candidates for the binding of transcription factors and are thus likely elements which confer expression patterns. Confirmation of these putative regulatory elements can be achieved by deletion analysis of each putative regulatory region followed by functional analysis of each deletion construct by assay of a reporter gene which is functionally attached to each construct. As such, once a starting promoter sequence is provided, any of a number of different functional deletion mutants of the starting sequence could be readily prepared.

As indicated above, fragments of a promoter also could be randomly prepared and then assayed. With this strategy, a series of constructs are prepared, each containing a different portion of the clone (a subclone), and these constructs are then screened for activity. A suitable means for screening for activity is to attach a promoter fragment to a selectable or screenable marker, and to isolate only those cells expressing the marker protein. In this way, a number of different promoter constructs are identified which still retain the desired, or even enhanced, activity. The smallest segment which is required for activity is thereby identified through comparison of the selected constructs. This segment may then be used for the construction of vectors for the expression of exogenous protein.

I. Recombinant Constructs and Transformation Vectors

One important application of the promoters provided by the invention will be in the construction of vectors designed for introduction into host cells by genetic transformation. Methods for preparing such vectors and components for their construction are known to those of skill of the art (see for example, Sambrook et al., 2001). The techniques of the current invention are thus not limited to any particular DNA sequences in conjunction with the promoter sequences provided herein. For example, the promoters alone could be transformed into a cell with the goal of enhancing or altering the expression of one or more genes in the host genome.

Transformation vectors can be used to direct the expression of a selected coding region encoding a particular protein or polypeptide product in a transgenic cell. In certain embodiments, a recipient cell may be transformed with more than one transformation construct. Two or more transgenes can also be introduced in a single transformation event using either distinct selected protein-encoding vectors, or using a single vector incorporating two or more gene coding sequences. Of course, any two or more transgenes of any description may be employed as desired.

Vectors used for transformation may include, for example, plasmids, cosmids, YACs (yeast artificial chromosomes), BACs (bacterial artificial chromosomes) or any other suitable cloning system, and the nucleic acids selected therefrom. It is contemplated that utilization of cloning systems with large insert capacities will allow introduction of large DNA sequences comprising more than one selected gene. Introduction of such sequences may be facilitated by use of bacterial or yeast artificial chromosomes (BACs or YACs, respectively).

Particularly useful for transformation may be expression cassette portions of vectors, isolated away from sequences not essential for expression in plants. DNA segments used for transforming cells will generally comprise the cDNA, gene or genes which one desires to introduced into and have expressed in the host cells. These DNA segments can further include, in addition to a promoter, structures such as promoters, enhancers, terminators, polylinkers, or even regulatory genes as desired. The DNA segment or gene chosen for cellular introduction may encode a protein which will be expressed in the resultant recombinant cells resulting in a screenable or selectable trait and/or which will impart an improved phenotype to the resulting transgenic cell or an organism. Alternatively, the vector may comprise a coding sequence for a protein or polypeptide which is to be isolated from the transgenic cells or is excreted from the transgenic cells. Exemplary components that may advantageously be used with transformation vectors are provided as follows.

A. Regulatory Elements

In addition to a promoter sequence of the invention, constructs prepared in accordance with the invention may comprise additional desired elements. For example, by including an enhancer sequence with such constructs, the expression of the selected protein may be enhanced. Enhancers often are found 5' to the start of transcription in a promoter that functions in eukaryotic cells, but can often be inserted in the forward or reverse orientation 5' or 3' to the coding sequence.

Where an enhancer is used in conjunction with a promoter for the expression of a selected protein, it will often be preferable to place the enhancer between the promoter and the start codon of the selected coding region. However, one also could use a different arrangement of the enhancer relative to other sequences and potentially still realize the beneficial properties conferred by the enhancer. For example, the enhancer could be placed 5' of the promoter region, within the promoter region, within the coding sequence (including within any intron sequences which may be present), or 3' of the coding region.

It also is contemplated that expression of one or more transgenes may be eliminated upon induction of the promoters provided herein. In particular, by operably linking a promoter to a coding sequence in antisense orientation, accumulation of the respective protein encoded by the sense transcript could be eliminated or decreased upon expression with the promoter.

B. Terminators

Transformation constructs prepared in accordance with the invention may include a sequence that acts as a signal to terminate transcription and allow for the poly-adenylation of the mRNA produced by coding sequences operably linked to a promoter of the invention. The termination sequence is preferably located in the 3' flanking sequence of a coding sequence, which will contain proper signals for transcription termination and polyadenylation. Many such terminator sequences are known to those of skill in the art. In constructing suitable expression constructs, the termination sequences associated with known genes from the host organism that are efficiently expressed in particular may be ligated into the expression vector 3' of the heterologous coding sequences to provide polyadenylation and termination of the mRNA.

C. Marker Genes

By employing a selectable or screenable marker gene as, or in addition to, a particular gene of interest, one can provide or enhance the ability to identify transformants. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker genes are known to the art and can be employed in the practice of the invention.

Included within the terms selectable or screenable marker genes also are genes which encode a "secretable marker" whose secretion can be detected as a means of identifying or selecting for transformed cells. Examples include marker genes which encode a secretable antigen that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., $\alpha$-amylase, $\beta$-lactamase, phosphinothricin acetyltransferase); and proteins that are inserted or trapped in the cell wall (e.g., proteins that include a leader sequence such as that found in the expression unit of extensin or tobacco PR-S).

Many selectable marker coding regions may be used in connection with a promoter of the present invention. Examples of selectable markers include neo (Potrykus et al., 1985), which provides kanamycin resistance and can be selected for using kanamycin, G418, paromomycin, etc.; bar, which confers bialaphos or phosphinothricin resistance; a nitrilase such as bxn from *Klebsiella ozaenae* which confers resistance to bromoxynil (Stalker et al., 1988) and a mutant acetolactate synthase (ALS) which confers resistance to imidazolinone, sulfonylurea or other ALS inhibiting chemicals (European Patent Application 154, 204, 1985) and a methotrexate resistant DHFR (Thillet et al., 1988).

Screenable markers that may be employed include a $\beta$-glucuronidase (GUS) or uidA gene, isolated from *E. coli*, which encodes an enzyme for which various chromogenic substrates are known; a $\beta$-lactamase gene (Sutcliffe, 1978), which encodes an enzyme for which various chromogenic substrates are known (e.g., PADAC, a chromogenic cephalosporin); a $\beta$-galactosidase gene, which encodes an enzyme for which there are chromogenic substrates; a luciferase (lux) gene (Ow et al., 1986), which allows for bioluminescence detection or a gene encoding for green fluorescent protein (Sheen et al., 1995; Haseloff et al., 1997; Reichel et al., 1996; Tian et al., 1997; WO 97/41228).

Other screenable markers provide for visible light emission as a screenable phenotype. A screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multi-well luminometry. It also is envisioned that this system may be developed for populational screening for bioluminescence. The gene which encodes green fluorescent protein (GFP) is contemplated as a particularly useful reporter gene (Sheen et al., 1995; Haseloff et al., 1997; Reichel et al., 1996; Tian et al., 1997; WO 97/41228). Expression of green fluorescent protein may be visualized in a cell as fluorescence following illumination by particular wavelengths of light.

The enzyme luciferase may be used as a screenable marker in the context of the present invention. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time. Another screenable marker which may be used in a similar fashion is the gene coding for green fluorescent protein.

D. Other Components

Sequences that are joined to the coding sequence of an expressed gene, which are removed post-translationally from the initial translation product and which facilitate the transport of the protein into or through intracellular or extracellular membranes, are termed transit or signal sequences. By facilitating the transport of the protein into compartments inside and outside the cell, these sequences may increase the accumulation of a gene product protecting the protein from intracellular proteolytic degradation. These sequences also allow for additional mRNA sequences from highly expressed genes to be attached to the coding sequence of the genes. Since mRNA being translated by ribosomes is more stable than naked mRNA, the presence of translatable mRNA 5' of the gene of interest may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

In general embodiments of the invention, a nucleic acid segment encoding a leader peptide sequence upstream and in reading frame with a selected coding sequence is used in recombinant expression of the coding sequence in a host cell. In certain aspects, a leader peptide sequence comprises a signal recognized by a host cell that directs the transport of a polypeptide expressed in accordance with the invention through the outer membrane of a cell or into the periplasmic space. In aspects wherein the secreted product is transported into the extracellular medium, that product may be readily purified from host cells. In some aspects, the leader sequences may be removed by enzymatic cleavage. Such leader peptide sequences and nucleic acids encoding the sequences are known in the art.

Additionally, vectors may be constructed and employed in the intracellular targeting of a specific gene product within the cells of a transgenic organism or in directing a protein to the extracellular environment. This generally will be achieved by joining a DNA sequence encoding a transit or signal peptide sequence to the coding sequence of a particular gene. An intracellular targeting DNA sequence may be operably linked 5' or 3' to the coding sequence depending on the particular targeting sequence. The resultant transit, or signal, peptide will transport the protein to a particular intracellular, or extracellular destination, respectively, and will then be post-translationally removed.

It may also be desired that a transformation construct comprises a bacterial origin of replication. One example of such an origin of replication is a colE1 origin. It also may be desirable to include a bacterial selectable marker in the vector, for example, an ampicillin, tetracyclin, hygromycin, neomycin or chloramphenicol resistance gene (Bolivar et al., 1977). The Ap gene is an example of an *E. coli* marker gene which has been cloned and sequenced and which confers resistance to beta-lactam antibiotics such as ampicillin (nucleotides 4618 to 5478 of GenBank accession number U66885). Constructs comprising such elements may advantageously be propagated in bacterial cells such as *E. coli* cells.

E. Vector Construction

Expression constructs preferably comprise restriction endonuclease sites to facilitate vector construction. Particularly useful are unique restriction endonuclease recognition sites. Examples of such restriction sites include sites for the restriction endonucleases NotI, AatII, SacII and PmeI. Endonucleases preferentially break the internal phosphodiester bonds of polynucleotide chains. They may be relatively unspecific, cutting polynucleotide bonds regardless of the surrounding nucleotide sequence. However, the endonucleases which cleave only a specific nucleotide sequence are called restriction enzymes. Restriction endonucleases generally internally cleave DNA molecules at specific recognition sites, making breaks within "recognition" sequences that in many, but not all, cases exhibit two-fold symmetry around a given point. Such enzymes typically create double-stranded breaks.

Many of these enzymes make a staggered cleavage, yielding DNA fragments with protruding single-stranded 5' or 3' termini. Such ends are said to be "sticky" or "cohesive" because they will hydrogen bond to complementary 3' or 5' ends. As a result, the end of any DNA fragment produced by an enzyme, such as EcoRI, can anneal with any other fragment produced by that enzyme. This properly allows splicing of foreign genes into plasmids, for example. Some restriction endonucleases that may be particularly useful with the current invention include HindIII, PstI, EcoRI, and BamHI.

Some endonucleases create fragments that have blunt ends, that is, that lack any protruding single strands. An alternative way to create blunt ends is to use a restriction enzyme that leaves overhangs, but to fill in the overhangs with a polymerase, such as klenow, thereby resulting in blunt ends. When DNA has been cleaved with restriction enzymes that cut across both strands at the same position, blunt end ligation can be used to join the fragments directly together. The advantage of this technique is that any pair of ends may be joined together, irrespective of sequence.

Those nucleases that preferentially break off terminal nucleotides are referred to as exonucleases. For example, small deletions can be produced in any DNA molecule by treatment with an exonuclease which starts from each 3' end of the DNA and chews away single strands in a 3' to 5' direction, creating a population of DNA molecules with single-stranded fragments at each end, some containing terminal nucleotides. Similarly, exonucleases that digest DNA from the 5' end or enzymes that remove nucleotides from both strands have often been used. Some exonucleases which may be particularly useful in the present invention include Bal31, S1, and ExoIII. These nucleolytic reactions can be controlled by varying the time of incubation, the temperature, and the enzyme concentration needed to make deletions. Phosphatases and kinases also may be used to control which fragments have ends which can be joined. Examples of useful phosphatases include shrimp alkaline phosphatase and calf intestinal alkaline phosphatase. An example of a useful kinase is T4 polynucleotide kinase.

Once the source DNA sequences and vector sequences have been cleaved and modified to generate appropriate ends they are incubated together with enzymes capable of mediating the ligation of the two DNA molecules. Particularly useful enzymes for this purpose include T4 ligase, *E. Coli* ligase, or other similar enzymes. The action of these enzymes results in the sealing of the linear DNA to produce a larger DNA molecule containing the desired fragment (see, for example, U.S. Pat. Nos. 4,237,224; 4,264,731; 4,273,875; 4,322,499 and 4,336,336, which are specifically incorporated herein by reference).

It is to be understood that the termini of the linearized plasmid and the termini of the DNA fragment being inserted must be complementary or blunt in order for the ligation reaction to be successful. Suitable complementarity can be achieved by choosing appropriate restriction endonucleases (i.e., if the fragment is produced by the same restriction endonuclease or one that generates the same overhang as that used to linearize the plasmid, then the termini of both molecules will be complementary). As discussed previously, in one embodiment of the invention, at least two classes of the vectors used in the present invention are adapted to receive the foreign oligonucleotide fragments in only one orientation.

After joining the DNA segment to the vector, the resulting hybrid DNA can then be selected from among the large population of clones or libraries.

F. Utilization of Expression Constructs

Introduction of expression vectors into host cells in accordance with the invention will find use for the introduction of one or more new traits to the host cell. One example of such a trait is the ability to produce a heterologous protein. Potentially any of the many techniques known in the art for introducing the vector DNA may be employed, whereby the host becomes capable of efficient expression of the inserted sequences. Such expression can be obtained by operably linking a promoter, coding sequence and sequence containing transcription termination signals (a "terminator"). That is, the promoter effects proper expression of the protein or, if a signal sequence is present, the signal sequence-protein complex and the terminator effects proper termination of transcription and polyadenylation. In case a signal sequence is used, the signal sequence is linked in the proper reading frame to the protein gene in such a manner that the last codon of the signal sequence is directly linked to the first codon of the gene for the protein. The signal sequence, if present, has its own ATG for translation initiation.

II. Modification of Plant Phenotypes

Modification of plant phenotypes requires use of promoters with appropriate expression profiles. Tissue-specific promoters may find use, for example, in modifying specific tissues within a plant while avoiding expression in other plant tissues, which may decrease plant productivity and/or complicate government regulatory approval. Alternatively, it may be desirable to use inducible promoters, for example, in the case of transgenes conferring resistance to environmental conditions such as phosphorous starvation, osmotic stress, pest attack such as insect predation, or other environmental stresses.

Many hundreds or even thousands of different plant and other coding sequences are known that may be operably linked to a promoter including those provided herein for expression in a plant. The promoters provided by the current invention may find use with any such sequence as well as newly isolated sequences. One example of a type of heterologous coding sequence that may find benefit for use in combination with a promoter sequence provided by the invention is a plant gene that, when expressed heterologously, results in increased plant phosphorous (P) utilization. For example, overexpression of certain plant acid phosphatases (APases) may be used to enhance the acquisition of phosphate from P sources that are normally largely inaccessible to plants, thus expanding the opportunities for engineering and breeding plants with enhanced phosphate metabolism efficiency. One such sequence is a purple acid phosphatase gene from *M. truncatula* (SEQ ID NO:28).

A phytase gene represents another type of gene that may be expressed for benefit in an inducible manner. Phytate can be hydrolyzed to inorganic phosphate (Pi) and myo-inositol through the action of phytase enzymes (Mudge et al., 2003). Phytases have been commercially produced based on the filamentous fungus *Aspergillus niger* (Brinch-Pedersen et al., 2002). By comparison, phytases in plant roots have received much less attention. Application of a fungal phytase to sterile cultures of subterranean clover (*Trifolium subterraneum*) enabled the seedlings to use phytate as the only source of P (Hayes et al., 2000). Ectopic expression of a fungal phytase gene (Richardson et al., 2001; Mudge et al., 2003) or a synthetic phytase gene (Zimmermann et al., 2003) resulted in increased P acquisition and biomass production in transgenic plants. A particularly useful example of a plant phytase is a novel phytase gene designated MtPHY1 isolated from model legume *Medicago truncatula* (SEQ ID NO:29), which is secreted as an extracellular enzyme in roots and thus may be used to increase plant capacity for P acquisition from phytate and improve plant growth.

III. Methods for Genetic Transformation

Suitable methods for transformation of plant or other cells for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by *Agrobacterium*-mediated transformation (U.S. Pat. No. 5,591,616 and U.S. Pat. No. 5,563,055; both specifically incorporated herein by reference) and by acceleration of DNA coated particles (U.S. Pat. Nos. 5,550,318; 5,538,877; and 5,538,880; each specifically incorporated herein by reference in its entirety), etc. Through the application of techniques such as these, the cells of virtually any plant species may be stably transformed, and these cells developed into transgenic plants.

A. *Agrobacterium*-Mediated Transformation

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

*Agrobacterium*-mediated transformation is most efficient in dicotyledonous plants and is the preferable method for transformation of dicots, including *Arabidopsis*, tobacco, tomato, alfalfa and potato. Indeed, while *Agrobacterium*-mediated transformation has been routinely used with dicotyledonous plants for a number of years, it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (Hiei et al., 1997; U.S. Pat. No. 5,591,616, specifically incorporated herein by reference in its entirety), wheat (McCormac et al., 1998), barley (Tingay et al., 1997; McCormac et al., 1998), alfalfa (Tomes et al., 1990) and maize (Ishidia et al., 1996).

Modem *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

B. Electroporation

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

C. Microprojectile Bombardment

Another method for delivering transforming DNA segments to plant cells in accordance with the invention is microprojectile bombardment (U.S. Pat. Nos. 5,550,318; 5,538,880; 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al., 1994), peanut (Singsit et al., 1997), cotton (McCabe and Martinell, 1993), tomato (VanEck et al., 1995), and legumes in general (U.S. Pat. No. 5,563,055, specifically incorporated herein by reference in its entirety).

D. Other Transformation Methods

Transformation of protoplasts can be achieved using methods based on calcium phosphate precipitation, polyethylene glycol treatment, electroporation, and combinations of these treatments (see, e.g., Potrykus et al., 1985; Lorz et al., 1985; Omirulleh et al., 1993; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts have been described (Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

To transform plant strains that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without protoplasting (Kaeppler, 1990; Kaeppler et al., 1992; U.S. Pat. No. 5,563,055, specifically incorporated herein by reference in its entirety). Transformation with this technique is accomplished by agitating silicon carbide fibers together with cells in a DNA solution. DNA passively enters as the cells are punctured. This technique has been used successfully with, for example, the monocot cereals maize (PCT Application WO 95/06128, specifically incorporated herein by reference in its entirety; (Thompson, 1995) and rice (Nagatani, 1997).

IV. Production and Characterization of Stably Transformed Plants

After effecting delivery of exogenous DNA to recipient cells, the next steps generally concern identifying the transformed cells and plants grown therefrom. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

A. Selection

It is believed that DNA is introduced into only a small percentage of target cells in any one experiment. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphostransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*. In the bacterial source organism, this enzyme acetylates the free amino group of PPT preventing auto-toxicity (Thompson et al., 1987). The bar gene has been cloned (Murakami et al., 1986; Thompson et al., 1987) and expressed in transgenic tobacco, tomato, potato (De Block et al., 1987) *Brassica* (De Block et al., 1989) and maize (U.S. Pat. No. 5,550,318). In previous reports, some transgenic plants which expressed the resistance gene were completely resistant to commercial formulations of PPT and bialaphos in greenhouses.

Another example of a herbicide which is useful for selection of transformed cell lines in the practice of the invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of mutations in the *Salmonella typhimurium* gene for EPSPS, aroA, which confer glyphosate resistance. The EPSPS gene was cloned from *Zea mays* and mutations similar to those found in a glyphosate resistant EPSPS were introduced in vitro. Mutant genes encoding glyphosate resistant EPSPS enzymes are described in, for example, International Patent WO 97/4103. The best characterized mutant EPSPS gene conferring glyphosate resistance comprises changes at codons for amino acid residues 102 and 106, although it is anticipated that other mutations will also be useful (PCT/WO97/4103).

An example of a screenable marker trait is the enzyme luciferase. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. These assays are nondestructive and transformed cells may be cultured further following identification. The photon counting camera is especially valuable as it allows one to identify specific cells or groups of cells which are expressing luciferase and manipulate those in real time. Another screenable marker which may be used in a similar fashion is the gene coding for green fluorescent protein.

It further is contemplated that combinations of screenable and selectable markers will be useful for identification of transformed cells. In some cell or tissue types a selection agent, such as bialaphos or glyphosate, may either not provide enough killing activity to clearly recognize transformed cells or may cause substantial nonselective inhibition of transformants and nontransformants alike, thus causing the selection technique to not be effective. It is proposed that selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. It is proposed that combinations of selection and screening may enable one to identify transformants in a wider variety of cell and tissue types. This may be efficiently achieved using a gene fusion between a selectable marker gene and a screenable marker gene, for example, between an NPTII gene and a GFP gene.

B. Regeneration and Seed Production

Cells that survive the exposure to the selective agent, or cells that have been scored positive in a screening assay, may be cultured in media that supports regeneration of plants. In one embodiment, MS and N6 media may be modified by including further substances such as growth regulators. One such growth regulator is dicamba or 2,4-D. However, other growth regulators may be employed, including NAA, NAA+ 2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, can then be allowed to mature into plants. Developing plantlets may be transferred to soiless plant growth mix, and hardened, e.g., in an environmentally controlled chamber, for example, at about 85% relative humidity, 600 ppm $CO_2$, and 25-250 microeinsteins $m^{-2} s^{-1}$ of light. Plants are preferably matured either in a growth chamber or greenhouse. Plants can be regenerated from about 6 wk to 10 months after a transformant is identified, depending on the initial tissue. During regeneration, cells may be grown on solid media in tissue culture vessels. Illustrative embodiments of such vessels are petri dishes and PLANTCONs. Regenerating plants are preferably grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with $10^{-5}$ M abscisic acid and then transferred to growth regulator-free medium for germination.

C. Characterization

To confirm the presence of the exogenous DNA or "transgene(s)" in the regenerating plants, a variety of assays may be performed. Such assays include, for example, "molecular biological" assays, such as Southern and Northern blotting and PCR; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

D. DNA Integration, RNA Expression and Inheritance

Genomic DNA may be isolated from cell lines or any plant parts to determine the presence of the exogenous gene through the use of techniques well known to those skilled in the art. Note, that intact sequences will not always be present, presumably due to rearrangement or deletion of sequences in the cell. The presence of DNA elements introduced through the methods of this invention may be determined, for example, by polymerase chain reaction (PCR). Using this technique, discreet fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR analysis. In addition, it is not typically possible using PCR techniques to determine whether transformants have exogenous genes introduced into different sites in the genome, i.e., whether transformants are of independent origin. It is contemplated that using PCR techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR, e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR, e.g., the presence of a gene.

Both PCR and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR techniques also may be used for detection and quantitation of RNA produced from introduced genes. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by northern blotting. This technique will demonstrate the presence of an RNA species and give information about the integrity of that RNA. The presence or absence of an RNA species also can be determined using dot or slot blot northern hybridizations. These techniques are modifications of northern blotting and will only demonstrate the presence or absence of an RNA species.

E. Gene Expression

While Southern blotting and PCR may be used to detect the gene(s) in question, they do not provide information as to whether the corresponding protein is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and $^{14}$C-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

V. Site Specific Integration or Excision of Transgenes

In one embodiment of the invention, techniques for the site-specific integration or excision of transformation constructs may be used. An advantage of site-specific integration or excision is that it can be used to overcome problems associated with conventional transformation techniques, in which transformation constructs typically randomly integrate into a host genome in multiple copies. This random insertion of introduced DNA into the genome of host cells can be lethal if the foreign DNA inserts into an essential gene. In addition, the expression of a transgene may be influenced by "position effects" caused by the surrounding genomic DNA. Further, because of difficulties associated with cells possessing multiple transgene copies, including gene silencing, recombination and unpredictable inheritance, it is typically desirable to control the copy number of the inserted DNA, often only desiring the insertion of a single copy of the DNA sequence.

Site-specific integration or excision of transgenes or parts of transgenes can be achieved in plants by means of homologous recombination (see, for example, U.S. Pat. No. 5,527, 695, specifically incorporated herein by reference in its entirety). Homologous recombination is a reaction between any pair of DNA sequences having a similar sequence of nucleotides, where the two sequences interact (recombine) to form a new recombinant DNA species. The frequency of homologous recombination increases as the length of the shared nucleotide DNA sequences increases, and is higher with linearized plasmid molecules than with circularized plasmid molecules. Homologous recombination can occur between two DNA sequences that are less than identical, but the recombination frequency declines as the divergence between the two sequences increases.

Introduced DNA sequences can be targeted via homologous recombination by linking a DNA molecule of interest to sequences sharing homology with endogenous sequences of the host cell. Once the DNA enters the cell, the two homologous sequences can interact to insert the introduced DNA at the site where the homologous genomic DNA sequences were located. Therefore, the choice of homologous sequences contained on the introduced DNA will determine the site where the introduced DNA is integrated via homologous recombination. For example, if the DNA sequence of interest is linked to DNA sequences sharing homology to a single copy gene of a host plant cell, the DNA sequence of interest will be inserted via homologous recombination at only that single specific site. However, if the DNA sequence of interest is linked to DNA sequences sharing homology to a multicopy gene of the host eukaryotic cell, then the DNA sequence of interest can be inserted via homologous recombination at each of the specific sites where a copy of the gene is located.

DNA can be inserted into the host genome by a homologous recombination reaction involving either a single reciprocal recombination (resulting in the insertion of the entire length of the introduced DNA) or through a double reciprocal recombination (resulting in the insertion of only the DNA located between the two recombination events). For example, if one wishes to insert a foreign gene into the genomic site where a selected gene is located, the introduced DNA should contain sequences homologous to the selected gene. A single homologous recombination event would then result in the entire introduced DNA sequence being inserted into the selected gene. Alternatively, a double recombination event can be achieved by flanking each end of the DNA sequence of interest (the sequence intended to be inserted into the genome) with DNA sequences homologous to the selected gene. A homologous recombination event involving each of the homologous flanking regions will result in the insertion of the foreign DNA. Thus only those DNA sequences located between the two regions sharing genomic homology become integrated into the genome.

Although introduced sequences can be targeted for insertion into a specific genomic site via homologous recombination, in higher eukaryotes homologous recombination is a relatively rare event compared to random insertion events. In plant cells, foreign DNA molecules find homologous sequences in the cell's genome and recombine at a frequency of approximately $0.5\text{-}4.2 \times 10^{-4}$. Thus any transformed cell that contains an introduced DNA sequence integrated via homologous recombination will also likely contain numerous copies of randomly integrated introduced DNA sequences. Therefore, to maintain control over the copy number and the location of the inserted DNA, these randomly inserted DNA sequences can be removed. One manner of removing these random insertions is to utilize a site-specific recombinase system. In general, a site specific recombinase system consists of three elements: two pairs of DNA sequence (the site-specific recombination sequences) and a specific enzyme (the site-specific recombinase). The site-specific recombinase will catalyze a recombination reaction only between two site-specific recombination sequences.

A number of different site specific recombinase systems could be employed in accordance with the instant invention, including, but not limited to, the Cre/lox system of bacteriophage P1 (U.S. Pat. No. 5,658,772, specifically incorporated herein by reference in its entirety), the FLP/FRT system of CaMV (Golic and Lindquist, 1989), the Gin recombinase of phage Mu (Maeser et al., 1991), the Pin recombinase of *E. coli* (Enomoto et al., 1983), and the R/RS system of the pSR1 plasmid (Araki et al., 1992). The bacteriophage P1 Cre/10× and the CaMV FLP/FRT systems constitute two particularly useful systems for site specific integration or excision of transgenes. In these systems, a recombinase (Cre or FLP) will interact specifically with its respective site-specific recombination sequence (10× or FRT, respectively) to invert or excise the intervening sequences. The sequence for each of these two systems is relatively short (34 bp for lox and 47 bp for FRT) and therefore, convenient for use with transformation vectors.

The FLP/FRT recombinase system has been demonstrated to function efficiently. Experiments on the performance of the FLP/FRT system indicate that FRT site structure, and amount of the FLP protein present, affects excision activity. In general, short incomplete FRT sites leads to higher accumulation of excision products than the complete full-length FRT sites. The systems can catalyze both intra- and intermolecular reactions in maize protoplasts, indicating its utility for DNA excision as well as integration reactions. The recombination reaction is reversible and this reversibility can compromise the efficiency of the reaction in each direction. Altering the structure of the site-specific recombination sequences is one approach to remedying this situation. The site-specific recombination sequence can be mutated in a manner that the product of the recombination reaction is no longer recognized as a substrate for the reverse reaction, thereby stabilizing the integration or excision event.

In the Cre-lox system, discovered in bacteriophage PI, recombination between loxP sites occurs in the presence of the Cre recombinase (see, e.g., U.S. Pat. No. 5,658,772, specifically incorporated herein by reference in its entirety). This system has been utilized to excise a gene located between two lox sites which had been introduced into a yeast genome (Sauer, 1987). Cre was expressed from an inducible GALI promoter and this Cre gene was located on an autonomously replicating yeast vector.

VI. Breeding Plants of the Invention

In addition to direct transformation of a particular plant genotype with constructs prepared according to the current invention, transgenic plants may be made by crossing a plant having a selected DNA of the invention to a second plant lacking the construct. For example, a selected DNA can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants. As used herein the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:

(a) plant seeds of the first (starting line) and second (donor plant line that comprises a transgene of the invention) parent plants;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking said desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

VII. Definitions

About: When used with respect to the length of a nucleic acid sequence, means plus or minus ten base pairs.

Expression cassette: A transformation construct from which non-essential portions have been removed prior to introduction into a host genome by genetic transformation. Preferred expression cassettes will comprise all of the genetic elements necessary to direct the expression of a selected gene. Expression cassettes prepared in accordance with the instant invention will include a promoter of the invention.

Expression: The combination of intracellular processes, including transcription and translation undergone by a coding DNA molecule such as a structural gene to produce a polypeptide.

Genetic Transformation: A process of introducing a DNA sequence or construct (e.g., a vector or expression cassette therefrom) into a cell in which that exogenous DNA is incorporated into a chromosome or is capable of autonomous replication.

Heterologous coding sequence: Any coding sequence other than the native coding sequence. A coding sequence is any nucleic acid sequence capable of being transcribed into an mRNA.

Promoter: A recognition site on a DNA sequence or group of DNA sequences that provides an expression control element for a structural gene and to which RNA polymerase specifically binds and initiates RNA synthesis (transcription) of that gene.

Selected DNA: A DNA segment which one desires to introduce into a genome by genetic transformation.

Selected Gene: A gene which one desires to have expressed in a transgenic cell or organism comprising such a cell. A selected gene may be native or foreign to a host genome, but where the selected gene is present in the host genome, will typically include one or more regulatory or functional elements which differ from native copies of the gene.

Transformation construct: A chimeric DNA molecule which is designed for introduction into a host genome by genetic transformation. Preferred transformation constructs will comprise all of the genetic elements necessary to direct the expression of one or more exogenous genes. Transformation constructs prepared in accordance with the instant invention will include a promoter of the invention. The term "transformation construct" specifically includes expression cassettes.

Transgene: A segment of DNA which has been incorporated into a host genome or is capable of autonomous replication in a host cell and is capable of causing the expression of one or more cellular products. Exemplary transgenes will provide the host cell, or organisms comprising such a cell, with a novel phenotype relative to the corresponding non-transformed cell or organism. Transgenes may be directly introduced into a cell genetic transformation, or may be inherited from a cell of any previous generation which was transformed with the DNA segment.

Transgenic cell: A cell or a progeny cell of any generation derived therefrom, wherein the DNA of the cell or progeny thereof contains an introduced exogenous DNA segment not originally present in a non-transgenic cell of the same strain. The transgenic cell may additionally contain sequences which are native to the cell being transformed, but wherein the "exogenous" gene has been altered in order to alter the level or pattern of expression of the gene.

Vector: A DNA molecule capable of replication in a host cell and/or to which another DNA segment can be operatively linked so as to bring about replication of the attached segment.

VIII. Examples

The following examples are included to illustrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Isolation of MtPT1 MtPT2 and MtPT3 Promoters and the Construction of Chimeric Transgenes For the isolation of MtPT1 promoter, the sequence information of MtPT1 cDNA (AF000354) was used to blast search genomic sequences of M. truncatula (www.genome.ou.edu/medicago.html), provided by the Advanced Center for Genome Technology of the University of Oklahoma (Roe and Kupfer, 2004). A contig containing the MtPT1 sequences was identified, and primers were designed to amplify M. truncatula genomic DNA to obtain 5' sequences of MtPT1 (FIG. 1). The MtPT1 promoter region was PCR amplified using primers 5' TATTATATGGATCCGCTGGAGTTC 3' (forward) (SEQ ID NO:4) and 5' CTCCAGCCATGGCTGAATTTGTT 3' (reverse) (SEQ ID NO:5). The forward primer contained a BamHI restriction site (underlined), and the reverse primer had a NcoI restriction site (underlined). The amplified sequence was digested by BamHI and NcoI, and the fragment was isolated after gel electrophoresis. The isolated MtPT1 promoter fragment (1535 bp, FIG. 1) was cloned into BamHI and NcoI digested binary vectors CaMV35S-GUS (pCAMBIA3301) and CaMV35S-GFP to replace the CaMV 35S promoter in front of the β-glucuronidase gene and GFP gene, respectively. The resulting gene constructs were designated MtPT1-GUS (FIG. 4A) and MtPT1-GFP (FIG. 4B).

For the isolation of the MtPT2 promoter, the MtPT2 cDNA (AF000355) was used to screen a genomic library of M. truncatula and a positive genomic clone was obtained. Direct sequencing of phage DNA isolated from the genomic clone was carried out to identify promoter regions of MtPT2. A 1156 bp intron was identified at position between −11 and −12 upstream of the translation initiation site. The MtPT2 promoter region was PCR amplified using primers 5' TTATTGAATTGGATCCCACTTGTC 3' (forward) (SEQ ID NO:6) and 5' TTACCATGGTCCCCAAGCTAGAGAG 3' (reverse) (SEQ ID NO:7). The reverse primer was designed at the flanking region between the intron and upstream regulatory sequences. The forward primer and reverse primer also contained a BamHI restriction site and NcoI restriction site, respectively. The isolated MtPT2 promoter fragment (FIG. 2) was cloned into BamHI and NcoI digested binary vectors CaMV35S-GUS and CaMV35S-GFP as described for MtPT1. The resulting gene constructs were named MtPT2-GUS (FIG. 4C) and MtPT2-GFP (FIG. 4D).

For the isolation of the MtPT3 promoter, the full-length MtPT3 cDNA sequence was used to BLAST search the M. truncatula genome sequence released by the Advanced Center for Genome Technology of the University of Oklahoma (www.genome.ou.edu/medicago.html). A M. truncatula clone mth2-1113 (AC122161) containing the MtPT3 and its regulatory sequences was identified. Two primers: MtPT3-promoter-1: 5' gtgatctgcaggtgcagcttgacaaccg 3' (forward) (SEQ ID NO:18) and MtPT3-promoter-2: 5' gtgg ccatggctccttgcaagaaaccaagttgat 3' (reverse) (SEQ ID NO:19) were used to obtain 1705 bp of MtPT3 promoter sequence from M. truncatula genomic DNA. The forward primer contains a PstI restriction site (underlined) and the reverse primer contained an NcoI restriction site (underlined). The PCR amplified MtPT3 promoter fragment was digested with both PstI and NcoI. The purified digested MtPT3 promoter fragment (1705 bp) was then ligated to a PstI and NcoI digested binary vector pCAMBIA3301. This results in the placement of the MtPT3 promoter in front of the P-glucuronidase gene. The resulting construct was designated MtPT3-GUS fusion construct (FIG. 4E).

Example 2

Transgenic Expression of Reporter Genes Under the Control of MtPT1 MtPT2 and MtPT3 Promoters A. *Agrobacterium*-Mediated Transformation The five new promoter-reporter gene constructs created as described above: MtPT1-GUS, MtPT1-GFP, MtPT2-GUS, MtPT2-GFP and MtPT3-GUS (FIG. 4A-E), were used for generating transgenic *Arabidopsis* plants and for hairy root transformation of *M. truncatula*. DNA of the binary vectors was transferred into the *Agrobacterium tumefaciens* strain C58 by the freeze-thaw method (Chen et al., 1994). Transgenic *Arabidopsis* plants were generated following the floral dip protocol method (Clough and Bent, 1998). The binary vectors were also transferred into *A. rhizogenes* strain Arqual (Quandt et al., 1993) and used for hairy root transformation of *M. truncatula* following the procedure described by Boisson-Dernier et al., (Boisson-Dernier et al., 2001). Transgenic *Arabidopsis* plants and transformed hairy roots of *M. truncatula* were grown at 24° C. under fluorescent light (240 μm$^{-2}$ s$^{-1}$) at a photoperiod of 16 h in the growth room.

B. Histochemical GUS Staining and GUS Activity Assay

Histochemical GUS staining was carried out on transgenic *Arabidopsis* plants and transformed *M. truncatula* hairy roots growing in modified MS agar medium containing 10 μM Pi. GUS expression pattern was visualized after incubating plantlets or roots in 100 mM sodium phosphate, pH 7.0, 10 mM Na-EDTA, 5 mM potassium ferricyanide, 5 mM potassium ferrocyanide, 0.3% (w/v) X-Gluc and 0.1% (v/v) Triton X-100 at 37° C. for 5 h (Mendel et al., 1989; Spangenberg et al., 1995).

Three-week-old transgenic *Arabidopsis* were grown on modified MS agar medium with various P concentrations (10 μM, 0.2 mM, 1 mM and 2 mM Pi). GUS enzyme activity was determined fluorometrically using the substrate 4-methylumbelliferyl A-D glucuronide (MUG) (Jefferson et al., 1987; Sessa et al., 1998). Briefly, tissues were ground in a mortar and pestle pre-cooled with liquid nitrogen, and the powder was transferred to a microcentrifuge tube containing 0.7 ml of extraction buffer [100 mM potassium phosphate (pH 7.8), 1 mM EDTA, 7 mM mercaptoethanol, 1% (v/v) Triton X-100, 10% (v/v) glycerol]. After 1 h incubation at room temperature, the tube was centrifuged at 14,000 rpm for 20 min at 4° C. The supernatant (300 µl) was transferred into a microcentrifuge tube containing 300 µl GUS buffer (extraction buffer containing 2 mM MUG) and fully mixed. 200 µl of this mixture was transferred into an eppendorf tube containing 1 ml of GUS stop buffer (0.2 M Na$_2$CO$_3$), stored at 4° C., and served as control. Another 200 µl of the mixture was incubated at 37° C. for 1 h and the reaction was stopped by adding 1 ml of GUS stop buffer. Fluorescence of the samples was read on a *Sequoia*-Turner Fluorimeter (Model 450) with emission at 455 nm and excitation at 365 nm. GUS enzyme activity was expressed as picomoles of 4-methylumbelliferone (MU) produced per minute per milligram of protein. Protein concentrations of the samples were determined using Bio-Rad Dc protein assay reagent (Bio-Rad Laboratories, Hercules, Calif.) with bovine serum albumin as standard. At least ten independent transgenic plants were analyzed, with triplicate samples collected for each transgenic plant. GUS activities of the transgenic plants were averaged and presented in graphs. In *Arabidopsis*, single insert T3 homozygous lines were used for the analysis. Significance of treatments was tested at the P=0.05 level. Standard errors are provided in all figures as appropriate.

C. GFP Observation Under Confocal Microscope

Hairy roots of *M. truncatula* and *Arabidopsis* plantlets transformed with GFP constructs were grown in modified MS agar medium with different Pi concentrations (10 µM, 0.2 mM, 1 mM and 2 mM). To study the reversibility of the transgene expression, 14-day-old transgenic *Arabidopsis* grown in 10 µM Pi conditions was transferred to high-P conditions (2 mM Pi) for two days, and then transferred back to 10 µM Pi conditions. GFP fluorescence was detected and imaged with the Bio-Rad 1024 ES Confocal Laser Scanning Microscope.

D. Cross Section Analysis of the Transformed Roots

*M. truncatula* hairy roots transformed with MtPT1-GUS and MtPT2-GUS were sectioned after histochemical GUS staining essentially following the procedure of Moll et al. (Moll et al., 2002). Briefly, the hairy roots were cut into small segments (approximately 0.5-1.0 cm) and immediately fixed for 1 h under reduced pressure in 4% (v/v) formaldehyde and 0.2% (v/v) glutaraldehyde in sample buffer (0.05 M potassium phosphate buffer, pH 7.2). The samples were then washed twice for 10 min in sample buffer, dehydrated in ethanol series, and embedded in paraffin wax. Sections (10 µM) were cut with a microtome, mounted on glass slides, and covered with thin glass cover after rehydration. Photographs were taken using an Olympus SZX stereomicroscope system with a SPOT RT color camera.

E. Results of Transgenic Expression of MtPT1 MtPT2 and MtPT3 Promoters

Figure 6:
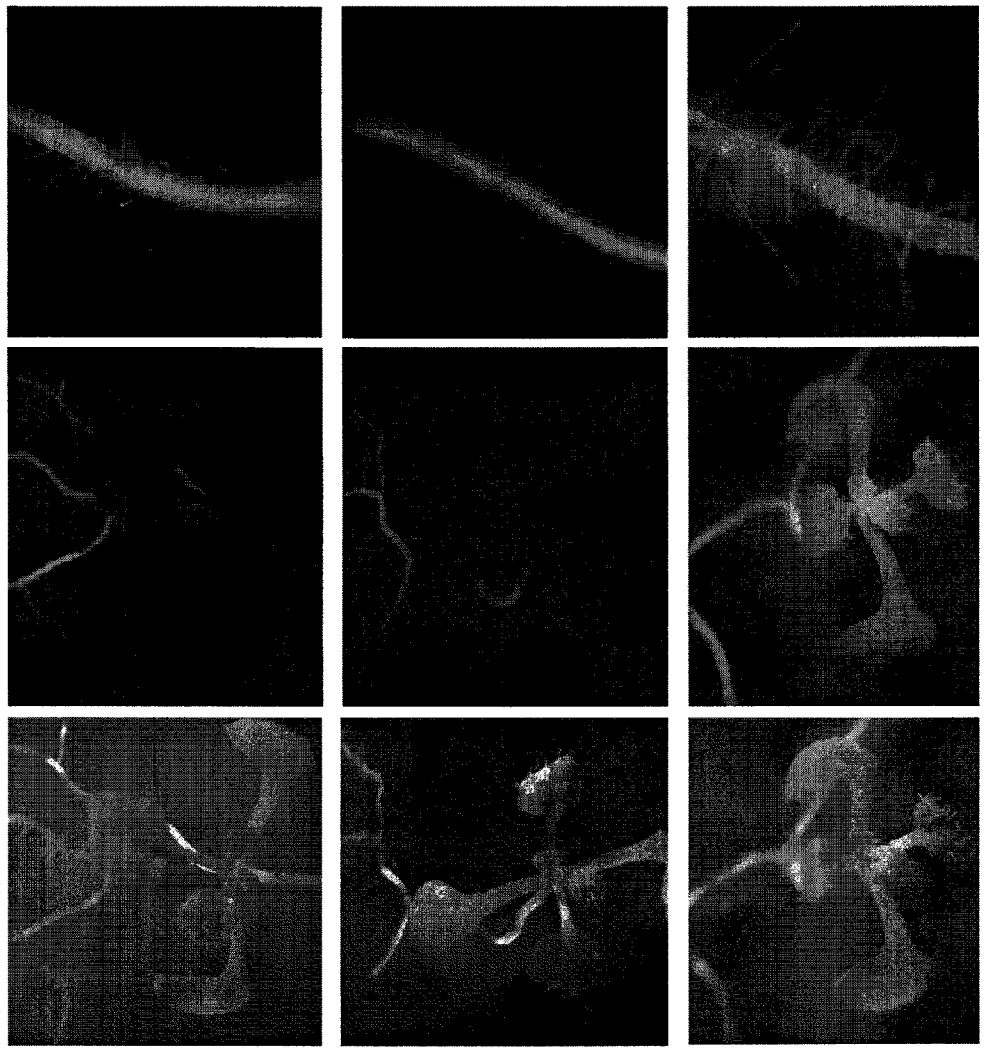
FIG. 6. Detection of GFP in transgenic Arabidopsis carrying MtPT1-GFP, MtPT2-GFP and constitutive promoter-GFP gene constructs, respectively. The Pi concentration in the growth medium was 10 µM.

The expression patterns of the reporter genes were compared in transgenic *Arabidopsis* bearing transgenes driven by different promoters. GUS staining of the transgenic plants carrying MtPT1-GUS and MtPT2-GUS transgenes revealed GUS expression only in root and root hairs (FIG. 5). Similarly, when GFP was driven by MtPT1 or MtPT2 promoters, fluorescence was only detectable in root and root hairs (FIG. 6). In contrast, CaMV35S driven reporter genes had expression in both shoot and root tissues (FIGS. 5, 6). Thus, MtPT1 and MtPT2 promoters led to root-specific expression in transgenic plants.

Figure 7:
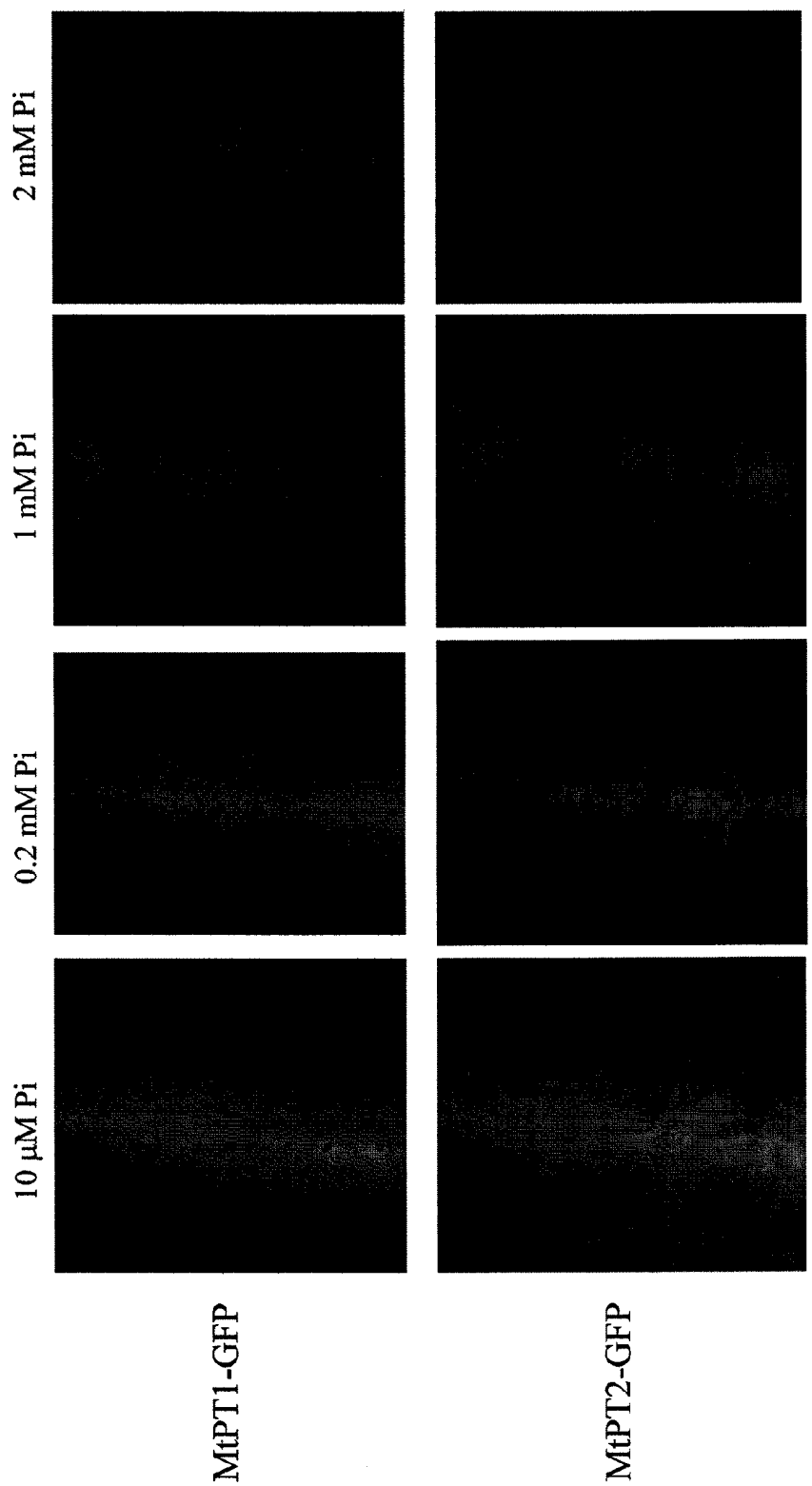
FIG. 7. Detection of GFP in transgenic Arabidopsis roots carrying MtPT1-GFP and MtPT2-GFP gene constructs under different Pi concentrations. The Pi concentrations in the growth media were 10 µM, 0.2 mM, 1 mM and 2 mM, respectively.

Expression levels of the reporter genes were evaluated under various Pi concentrations: 10 µM, 0.2 mM, 1 mM and 2 mM. In transformed *M. truncatula* hairy roots carrying MtPT1-GFP and MtPT2-GFP, decreasing levels of GFP fluorescence was observed with increasing Pi concentrations for both promoters (FIG. 7). Similarly, in transgenic *Arabidopsis* roots carrying MtPT1-GUS (FIG. 8A) and MtPT2-GUS (FIG. 8B), a significant reduction in GUS activity was found when roots were growing in 0.2 mM Pi instead of 10 µM Pi, and further reductions were observed when transgenic roots were growing under 1 mM and 2 mM Pi conditions (FIG. 8). Thus, both MtPT1 and MtPT2 promoters were inducible by reduced levels of Pi. The expression of the transgenes under MtPT1 and MtPT2 promoters were not affected by two other major nutrients N and K.

In transformed *M. truncatula* roots expressing the MtPT3-GUS fusion construct, strong GUS staining was evident exclusively in the vascular tissues (FIG. 15A-C). This expression pattern is in constrast to that seen for MtPT1 promoter-reporter gene fusion constructs and partially overlaps with the pattern observed for the MtPT2 promoter-reporter gene fusion constructs. In the MtPT3-GUS roots, GUS staining was visible in the vascular tissue of roots of plants fertilized with 2 mM phosphate (FIG. 15A-C) and was substantially stronger in plants fertilized with 10 µM phosphate indicating that the promoter responds to the phosphate status of the plant.

Example 3

Deletion Analysis of MtPT1 and MtPT2 Promoters

To further characterize the MtPT1 promoter, a series of deletions of the promoter region were created by PCR using the primers D1 (5' AGGTAGGATCCTTTATAGTTTTG 3') (SEQ ID NO:8), D2 (5' GCAAGAGGTA GGATCCCTATCTA 3') (SEQ ID NO:9), D3 (5' GCTTGT GGATCCTTGACATTGGT 3') (SEQ ID NO:10), D4 (5' AACCTCGGATCCGCGTAAGCAT 3') (SEQ ID NO:11) at the 5' end and Rev (5' CTCCAGCCATGGCTGAATTTGTT 3') (SEQ ID NO:12) at the 3' end (FIG. 1). A BamHI restriction site was introduced in the forward primers, and a NcoI restriction site was introduced in the reverse primer. The shortened promoter sequences obtained after PCR amplification were digested by BamHI and NcoI, and were cloned into BamHI and NcoI digested binary vector CaMV35S-GUS to drive the GUS gene.

Similarly, a series of deletions of the MtPT2 promoter were created by PCR using the primers D1 (5' GCAA GGATCCTGTTACCTATAT 3') (SEQ ID NO:13), D2 (5' ACTAGGATCCAGATTTAAGAAA3') (SEQ ID NO:14), D3 (5' AGGATCCATCCCGAAATTATGC 3') (SEQ ID NO:15), D4 (5' CCACAAGTGGATCCAATGTCAAA 3') (SEQ ID NO:16) at the 5' end and Rev (5' TTA CCATGGTCCCCAAGCTAGAGAG 3') (SEQ ID NO:17) at the 3' end (FIG. 2). The shortened promoter sequences obtained after PCR were cloned into BamHI and NcoI digested CaMV35S-GUS to drive the GUS gene. Transgenic *Arabidopsis* plants were generated using GUS gene constructs driven by the shortened MtPT1 promoter segments generated (FIG. 1). Under low-Pi conditions, shortening the promoter sequence down to 975 bp (SEQ ID NO:20) reduced GUS activity in roots, although overall expression was still strong (FIG. 12). Deletion of the sequence to 551 bp (SEQ ID NO:21) further reduced GUS activity in root (FIG. 12) and changed the expression pattern (FIG. 13A). Under the control of the 551 bp fragment, GUS expression was no longer limited to root (FIG. 13A) and activity in leaf was drastically increased (FIG. 14A), but promoter activity was observed.

Thus the sequence between 875 bp and 551 bp was indicated to play a role in root specificity of gene expression. Further shortening the sequence to 342 bp (SEQ ID NO:22) resulted in a reduction of GUS activity to the same level measured under high-Pi conditions and a nearly 1:1 ratio of GUS activity under high- and low-Pi conditions (FIG. 12A), indicating that the fragment between 551 bp and 342 bp is possibly related to Pi inducibility. In the case of the 133 bp fragment (SEQ ID NO:23), expression was greatly reduced, but promoter activity was nonetheless observed (FIG. 12A). Shortening the MtPT2 promoter sequence to 962 bp (SEQ ID NO:24) had no effect on gene expression (FIGS. 12B, 13B). Deletion of the sequence to 586 bp (SEQ ID NO:25) and 266 bp (SEQ ID NO:26) resulted in significant reductions in GUS activities under low-Pi conditions, but also drastic increase in GUS expression in leaf tissues (FIGS. 13B, 14B), suggesting the presence of root specificity related regulatory elements between 962 and 586 of the promoter sequence. GUS activity was greatly reduced in the case of the 126 bp fragment (SEQ ID NO:27), but activity was observed (FIG. 12B).

Example 4

Reversibility of Transgene Expression Under the Control of the MtPT1 and MtPT2 Promoters Transgenic *Arabidopsis* growing at low-Pi (10 μM) conditions were transferred to high-Pi (2 mM) conditions, and then transferred back to low-Pi conditions. GFP fluorescence in roots was substantially reduced when plants were transferred to high-Pi conditions, but the expression was resumed after transfer the plants to low-Pi conditions (FIG. 9). Measurement of GUS activities in roots of MtPt1-GUS plants revealed a 10-fold reduction after transferring transgenic plants to high Pi conditions, however, when the plants were transferred back to low Pi conditions, GUS expression reversed back to the original level (FIG. 10A). Measurement of GUS activities in roots of MtPt2-GUS plants showed that transgene expression was similar in MtPT1-GUS, expression level under the control of MtPT2 promoter was also reversible (FIG. 10B).

Example 5

Differences in Transgene Expression Driven by MtPT1, MtPT2 and MtPT3 Promoters

The tissue-specific expression pattern of MtPT1, MtPT2 and MtPT3 was further analyzed by localizing reporter gene expression in transformed roots of *M. truncatula*. Cross section and longitudinal section of GUS expressing roots revealed distinct differences in the patterns of reporter gene driven by the MtPT1, MtPT2 and MtPT3 promoters. The expression of GUS driven by MtPT1 promoter was mainly in root epidermal cells and in cortex cells, but not in the vascular cylinder in the center of roots (FIG. 1A-B). In contrast, MtPT2 promoter driven GUS not only had expression in epidermis and cortex, but showed stronger expression in vascular tissues in the center of roots (FIG. 11C-D). Finally, when the GUS gene was expressed under the control of the MtPT3 promoter, GUS staining was seen exclusively in the vascular cylinder (FIG. 15A-C).

Example 6

Identification of Motifs in MtPT1 and MtPT2 Promoters

The MtPT1 and MtPT2 promoter sequences were analyzed by PLACE program (Higo et al., 1999) to identify DNA elements which may be involved in gene regulation. The PIBS motif (GNATATNC; SEQ ID NO:30), an element associated with Pi starvation signalling in *Arabidopsis* (Rubio et al., 2001) was identified in the MtPT1 and MtPT2 promoters, respectively. The root motif box (ATATT; SEQ ID NO:31) is repeated 20 and 13 times in MtPT1 and MtPT2 promoters, respectively. Additional motifs identified in MtPT1 and/or MtPT2 promoters are diverse in their putative functions, being associated with light response (-10PEHVPSB; Thum et al., 2001); phytochrome regulation (REBETALGL-HCB21; Degenhardt and Tobin, 1996), low temperature response (LTR1HVBLT49; Dunn et al., 1998), or water stress response (MYBCORE; Luscher, 1990; Urao et al., 1993). The PHO and PHO-like elements found in Pi starvation-induced genes (Mukatira et al., 2001; Hammond et al., 2003; Schunmann et al., 2004) are not present in the MrPT1 and MtPT2 promoters.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for, or teach methodology, techniques, and/or compositions employed herein.

U.S. Pat. No. 4,237,224
U.S. Pat. No. 4,264,731
U.S. Pat. No. 4,273,875
U.S. Pat. No. 4,322,499
U.S. Pat. No. 4,336,336
U.S. Pat. No. 4,535,060
U.S. Pat. No. 5,302,523
U.S. Pat. No. 5,322,783
U.S. Pat. No. 5,384,253
U.S. Pat. No. 5,464,765
U.S. Pat. No. 5,508,184
U.S. Pat. No. 5,527,695
U.S. Pat. No. 5,538,877
U.S. Pat. No. 5,538,880
U.S. Pat. No. 5,545,818
U.S. Pat. No. 5,550,318
U.S. Pat. No. 5,563,055
U.S. Pat. No. 5,591,616
U.S. Pat. No. 5,610,042
U.S. Pat. No. 5,658,772
Abdullah et al., *Biotechnology*, 4:1087, 1986.
Araki et al., *J. Mol. Biol.*, 225(1):25-37, 1992.
Bates, *Mol. Biotechnol.*, 2(2):135-145, 1994.
Battraw and Hall, *Theor. App. Genet.*, 82(2):161-168, 1991.
Bhattacharjee et al., *J. Plant Bioch. Biotech.*, 6(2):69-73. 1997.

Boisson-Dernier et al., *Mol. Plant. Microbe Interact.*, 14:695-700, 2001.
Bolivar et al., *Proc. Natl. Acad. Sci. USA*, 74(12):5265-5269, 1977.
Bower et al., *J. Plant*, 2:409-416. 1992.
Brinch-Pedersen et al., *Trends Plant Sci.*, 7(3):118-125, 2002.
Buising and Benbow, *Mol. Gen. Genet.*, 243(1):71-81, 1994.
Callis et al., *Genes Dev.*, 1: 1183-1200, 1987.
Casa et al., *Proc. Natl. Acad. Sci. USA*, 90(23):11212-11216, 1993.
Chen et al., *Biotechniques*, 16:664-670, 1994.
Christou et al., *Proc. Natl. Acad. Sci. USA*, 84(12):3962-3966, 1987.
Clough and Bent, *Plant J.*, 16:735-743, 1998.
D'Halluin et al, *Plant Cell*, 4(12):1495-1505, 1992.
DE Appln. 3642 829A
De Block et al., *Plant Physiol.*, 91:694-701, 1989.
De Block et al., *The EMBO Journal*, 6(9):2513-2518, 1987.
Enomoto, et al., *J. Bacteriol.*, 6(2):663-668, 1983.
European Pat. Appln. 154,204
Fraley et al., *Bio/Technology*, 3:629-635, 1985.
Fromm et al., *Nature*, 319:791-793, 1986.
Ghosh-Biswas et al., *J. Biotechnol.*, 32(1):1-10, 1994.
Golic and Lindquist, *Cell*, 59:3, 499-509. 1989.
Hagio et al., *Plant Cell Rep.*, 10(5):260-264, 1991.
Haseloff et al., *Proc. Natl. Acad. Sci. USA*, 94(6):2122-2127, 1997.
Hayes et al., *Plant Soil*, 220:165-174, 2000.
He et al., *Plant Cell Reports*, 14 (2-3):192-196, 1994.
Hensgens et al., *Plant Mol. Biol.*, 22(6):1101-1127, 1993.
Hiei et al., *Plant. Mol. Biol.*, 35(1-2):205-218, 1997.
Hou and Lin, *Plant Physiology*, 111:166, 1996.
Ishidia et al., *Nat. Biotechnol.*, 14(6):745-750, 1996.
Jefferson et al., EMBO J., 6:3901-3907, 1987.
Kaeppler et al., *Plant Cell Reports*, 9:415-418, 1990.
Kaeppler et al., *Theor. Appl. Genet.*, 84(5-6):560-566, 1992.
Klee et al., *Bio-Technology*, 3(7):637-642, 1985.
Knittel et al., *Plant Cell Reports*, 14(2-3):81-86, 1994.
Kunkel et al., *Methods Enzymol.*, 154:367-382, 1987.
Lazzeri, *Methods Mol Biol*, 49:95-106, 1995.
Lee et al., *Environ. Mol. Mutagen.*, 13(1):54-59, 1989.
Lorz et al., *Mol Gen Genet*, 199:178-182, 1985.
Maeser et al, *Mol. Gen. Genet.*, 230(1-2):170-176, 1991.
Marcotte et al., *Nature*, 335:454, 1988.
McCabe and Martinell, *Bio-Technology*, 11(5):596-598, 1993.
McCormac et al., *Euphytica*, 99(1):17-25, 1998.
Mendel et al., *Theor. Appl. Genet.*, 78:31-34, 1989.
Moll et al., *Plant Physiol.*, 130: 47-57, 2002.
Mudge et al., *Plant J.*, 31:341-353, 2002.
Mudge et al., *Plant Sci.*, 165:871-878, 2003.
Murakami et al., *Mol. Gen. Genet.*, 205:42-50, 1986.
Nagatani et al., *Biotech. Tech.*, 11(7):471-473, 1997.
Ogawa et al., *Sci. Rep.*, 13:42-48, 1973.
Omirulleh et al., *Plant Mol. Biol.*, 21(3):415-28, 1993.
Ow et al., *Science*, 234:856-859, 1986.
PCT Appln. WO 92/17598
PCT Appln. WO 94/09699
PCT Appln. WO 95/06128
PCT Appln. WO 97/4103
PCT Appln. WO 97/41228
Potrykus et al., *Mol. Gen. Genet.*, 199:183-188, 1985.
Quandt et al., *Mol. Plant-Microbe Interact.*, 6:699-706, 1993.
Reichel et al., *Proc. Natl. Acad. Sci. USA*, 93 (12) p. 5888-5893. 1996
Rhodes et al, *Methods Mol. Biol.*, 55:121-131, 1995.
Richardson et al., *Plant J.*, 25:641-649, 2001.
Ritala et al., *Plant Mol. Biol.*, 24(2):317-325, 1994.
Roe and Kupfer, In Molecular Breeding of Forage and Turf, Hopkins et al., (Eds.), Kluwer Academic Publishers, Dordrecht, 333-344, 2004.
Rogers et al., *Methods Enzymol.*, 153:253-277, 1987.
Sambrook et al., In: *Molecular cloning*, Cold Spring Harbor Laboratory Press, Cold Spring Harbor, N.Y., 2001.
Sauer, *Mol. and Cell. Biol.*, 7: 2087-2096. 1987.
Schachtman et al., *Plant Physiol.*, 116:447-453, 1998.
Sessa et al., *Plant Mol. Biol. Rep.*, 16:191-197, 1998.
Sheen et al., *Plant Journal*, 8(5):777-784, 1995.
Singsit et al., *Transgenic Res.*, 6(2):169-176, 1997.
Spangenberg et al., *J. Plant Physiol.*, 145:693-701, 1995.
Spencer et al., *Plant Molecular Biology*, 18:201-210, 1992.
Stalker et al., *Science*, 242:419-422, 1988.
Sutcliffe et al., *Rev Drug Metab Drug Interact.*, 5(4):225-272, 1987.
Thillet et al., *J. Biol. Chem.*, 263:12500-12508, 1988.
Thompson et al., *Euphytica*, 85(1-3):75-80, 1995.
Thompson et al., *The EMBO Journal*, 6(9):2519-2523, 1987.
Tian et al., *Genes Dev.*, 111(1):72-82, 1997.
Tingay et al., *Plant J*, 11(6):1369-1376, 1997.
Tomes et al, *Plant. Mol. Biol.*, 14(2):261-268, 1990.
Tomic et al., *Nucleic Acids Res.*, 18(6): 1656, 1990.
Torbet et al., *Crop Science*, 38(1):226-231, 1998.
Torbet et al., *Plant Cell Reports*, 14(10):635-640, 1995.
Toriyama et al., *Theor Appl. Genet.*, 73:16, 1986.
Tsukada et al., *Plant Cell Physiol.*, 30(4)599-604, 1989.
Uchimiya et al., *Mol. Gen. Genet.*, 204:204, 1986.
Upender et al., *Biotechniques.*, 18(1):29-30, 32, 1995.
Van Eck et al., *Plant Cell Reports*, 14(5):299-304, 1995.
Vance et al., *New Phytol.*, 157:423-447, 2003.
Vasil et al., *Plant Physiol.*, 91:1575-1579, 1989.
Yamada et al., *Plant Cell Rep.*, 4:85, 1986.
Zheng and Edwards, *J. Gen. Virol.*, 71:1865-1868, 1990.
Zhou et al., *Exp. Hematol*, 21:928-933, 1993.
Zimmermann et al. *Plant Biotechnol. J.*, 1:353-360, 2003.
Higo et al., *NAR* 27:297-300, 1999.
Rubio et al., *Genes Dev.* 15:2122-2133, 2001.
Thum et al., *Plant Mol. Biol.* 47:353-366, 2001.
Degenhardt and Tobin, *Plant Cell* 8:31-41, 1996.
Dunn et al., *Plant Mol. Biol.* 38:551-564, 1998.
Luscher, *Genes Dev.* 4:2235-2241, 1990.
Urao et al., *Plant Cell* 5:12529-1539, 1993.
Mukatira et al., *Pl. Physiol.* 127:1854-1862, 2001.
Hammond et al. *Pl. Physiol.* 132:578-596, 2003
Schunmann et al., *Pl. Physiol.* 136:4205-4214, 2004.

What is claimed is:

1. A nucleic acid sequence selected from the group consisting of:
   (a) a nucleic acid sequence comprising the nucleic acid sequence of SEQ ID NO:2, or a fragment thereof having promoter activity, wherein said fragment comprises SEQ ID NO:26;
   (b) a nucleic acid sequence that hybridizes to the nucleic acid sequence of (a) under conditions of 5×SSC, 50% formamide and 42° C., wherein the isolated nucleic acid sequence has promoter activity;
   (c) a nucleic acid sequence having at least 98% sequence identity to the nucleic acid sequence of SEQ ID NO:2, or a fragment thereof having promoter activity, wherein said fragment comprises SEQ ID NO:26, wherein the nucleic acid sequence has promoter activity; and
   (d) the complement of any of (a)-(c),
   wherein said nucleic acid sequence is operably linked to a heterologous coding sequence.

2. The nucleic acid sequence of claim 1, further defined as operably linked to an enhancer.

3. The nucleic acid sequence of claim 1, further defined as comprising a nucleic acid sequence of SEQ ID NO:24, SEQ ID NO:25 or SEQ ID NO:26.

4. A transformation construct comprising the nucleic acid sequence of claim 1 operably linked to a heterologous coding sequence.

5. The transformation construct of claim 4, wherein the coding sequence is operably linked to a terminator.

6. The transformation construct of claim 4, further comprising an enhancer.

7. The transformation construct of claim 4, further comprising a selectable marker.

8. The transformation construct of claim 4, further comprising at least a second promoter.

9. The transformation construct of claim 8, further comprising at least a second heterologous coding sequence operably linked to said second promoter.

10. The transformation construct of claim 4, further comprising a screenable marker.

11. A plant transformed with a selected DNA comprising the nucleic acid sequence of claim 1.

12. The plant of claim 11, further defined as a dicotyledonous plant.

13. The plant of claim 11, further defined as a monocotyledonous plant.

14. A cell of the plant of claim 11.

15. A seed of the plant of claim 11, wherein said seed comprises said selected DNA.

16. A progeny plant of any generation of the plant of claim 11, wherein said progeny plant comprises said selected DNA.

17. A method of expressing a polypeptide in a plant cell comprising the steps of:
   (a) obtaining a construct comprising the nucleic acid sequence of claim 1 operably linked to a heterologous coding sequence encoding a polypeptide; and
   (b) transforming a recipient plant cell with the construct, wherein said recipient plant cell expresses said polypeptide.

18. The method of claim 17, wherein the plant cell is further defined as a dicotyledonous plant cell.

19. The method of claim 17, wherein the plant cell is further defined as a monocotyledonous plant cell.

20. A method of producing a plant transformed with a selected DNA comprising the nucleic acid sequence of claim 1 operably linked to a heterologous coding sequence, comprising:
   (a) obtaining a first plant comprising said selected DNA;
   (b) crossing said first plant to a second plant lacking said selected DNA; and
   (c) obtaining at least a first progeny plant resulting from said crossing,
   wherein said progeny plant has inherited said selected DNA.

21. The method of claim 20, wherein the plant is further defined as a dicotyledonous plant.

22. The method of claim 20, wherein the progeny plant is a monocotyledonous plant.

* * * * *

SEQUENCE LISTING

<160> NUMBER OF SEQ ID NOS: 31

<210> SEQ ID NO 1
<211> LENGTH: 1533

```
<212> TYPE: DNA
<213> ORGANISM: Medicago truncatula

<400> SEQUENCE: 1
gctggagttc gaatcccgaa caccccactt ctccacattt aaaatgtgtg aactcaagtc      60
actatgttat ttgaccaaaa aaacaaaatg agaaaaaaaa agaccaagcg gggaaaagta     120
cccatttacc aagtcgatac aaatactaat tgactttat tttttggtta aaaataataa      180
ttgactttt ttaggggaaa taataataat tgacattttt tttttaatat ttttgacaaa      240
aaattgactt tatgtaccga ttataattat cataaaccca cataatataa cgtcatagtt     300
taattgacag ttggtctgaa acaaaatata gtttaacttg ttagtttttt tagaggagtt     360
aaattgccag ttggttgcat tgcataaat ggcgcatgca cgagttgata tatactattt      420
gatttgataa gagtatacga tacttgtacg ttttgtactt gtgatatatt atgttattgc     480
ggaatatttt atgaaaaat ttatggttga cattcaaact aaaatgttta cttaatggta      540
gagttataaa cctcgggtcc gcgtaagcat agctcagttg gcagagacat gcattattat     600
atgtaggggc tggggttcaa accccggaca ccccacttat tcatcttgaa aaatatgaat     660
tctaaccact aaaattacttg accaaaataa cccaaaatcc tgatgtagga gatcctctga    720
ttaatgtata attttgaaa gaatgtataa catatagttg aatattaggt tgcaacagat      780
acaagggta ttaaatatat tgagcatatc ctcaagtgga atcaatgtca aatctgaaat      840
atcgtttaat ttccttaacg gatgtcctat atttttcatt ggttatgtct atgtattaag     900
aatatattac ttaaaaacta taaattaatt agagtccaac ttaaaatttt attaagttac     960
aaaaaatagt gcttgtgaag cgttgacatt ggtgaatgct tatgattaat taggcatata    1020
ccccattgat gctaaattga ttctttttga ctttggatgc attcctgatt tggctaggat    1080
tgttacctat atatagctga gtttgattat ctgctcacag tgtgcataaa cctagcttct    1140
cataccactt tacttcttta tcaacttggc ttccttgcaag aggtacgaac tctatctatc    1200
tcccttattg agtttgtaga caccaaatga gtattcatgt tgtacatttt tttttggcaa    1260
atcttggtcg catcatacaa ctgtagagat taatggctcg agataactaa gatatattta    1320
aagagtttag tactcgagtg tatgtgtgta taaaaatata tataattttc attggtatta    1380
ggcacaattt aggtaggtta ctttatagtt ttgagcagtt tatccatttc ttacctcagc    1440
ctcacaaatg tcaagttagt ttttttttg tttactaata tttaatgtgt cttgtgctta    1500
attatgcagg gaaaaactag gtaacaaatt cag                                 1533

<210> SEQ ID NO 2
<211> LENGTH: 1238
<212> TYPE: DNA
<213> ORGANISM: Medicago truncatula

<400> SEQUENCE: 2
ccacttgtct ttattttta agggcaggga ccaccttgtt atttgcttaa aattgaacga      60
aaatattaag attatagtct ctttaggatt acttaaaaaa tcaacaagca aactatgaat    120
ggataattta tgatatagca aatagaaac tattatacaa acccagaatt ttgttattgg     180
agaacctcta actaccagta tagttgaata ttgggttgca acagatacaa ggggtattaa    240
atatattgag catatatctg tttccacaag tggaatcaat gtcaaatcta aaaaatatct    300
cttaattacc ttaagtggaa tggatgtcct agatttttaa ttggttatgt atctgtatta    360
aggatatatt actcggaaag aataaattag catgtgaact attatagttc cctaaaaaaa    420
aaagtcaact attatagtgg ttttcctcta aaaagagag taaattacac ttcgctttcc    480
```

-continued

```
ttacagatgt tgaattact gttccatctc ctcttatatt aaaatataca ttttattctc      540
ctcttattca aaacatatta tgctaaaaaa aaaatctatt agggattttg aatcgttgaa      600
caacataatt gttttactta agtcttaagg tgtttaaatc tctttaggtc aacatcccga      660
aattatgctt aagcatgttt aaatttgtga ttaatgaaat tactttggtg attagctagt      720
gaatttcaac tcttgatata tccaatagca attgccgcaa aagttgtata aatttagttg      780
tacaaatatc atttatctat aatacatttt tcattcctaa ttttatatca aataaacatg      840
gttggatgca agtgatttac atgtgtttcc tattatttat ttacattttt tattacaatg      900
atgtatgtgt ttctgttaat gttgaatgct tagggtatcc aagtttaatc attaattaac      960
ataactagca ttcagattta agaaacaaga aaattaatta aaaaaaaaat agtgcttata     1020
aagcgtttac attgatgaat gcttgtgagt ggtgattagg ttaggcatat accattgatg     1080
ctgaattgat tcctttgacc tagcaaggtt catgttacct atatatatgc atattaatag     1140
tttagctgct caaagtgcag gcacctagct agctcctcat acaaacttga cttctcacaa     1200
ggaggtcttc tctctctcta tctctctagc ttggggac                             1238
```

<210> SEQ ID NO 3  
<211> LENGTH: 1705  
<212> TYPE: DNA  
<213> ORGANISM: Medicago truncatula

<400> SEQUENCE: 3

```
gtgatctgca ggtgcagctt gacaaccgac taggttagaa tatcacattg accttatcac       60
ttatatagtg tacctaagat aaataaatgc gacattactg ttacttaata tccaacaata      120
taaacagggt ggattcgaat cctaaccgct gcttactttt ctgcaaccaa aaataggtaa      180
acttgctctg ttgcaatcag ataaaaattg caagacatct aacccttata ttttatatcg      240
tcaacttaca aaaataagta acaagaattg tttggacgaa acgactttcc ttttggatac      300
gatactctac ttatcagttt attacttgtt aaacgatttg gtacactggc gacattcgac      360
catcatagag ctctagcgtc gacacgatta tgagttagcc tcaatctggt ttttgctatg      420
ttttgttagt ttctgtttat ttgcatttgt ttttattttg ttcagtggag atgaagatgg      480
gtggtggctt tgtttcggct atgtgatttg gtatgaaaat cttgaatctg atttctgaa      540 ttaatgatat gggttcttta tttagggtgt tgttctgttg gatgcatatc tcgattcaac      600
atgactgctt ttatcctaat gttgcttgaa agggttagtt gcgtagatgc cccgtgttga      660
tggtagtagt cgttcatcgt acctaaagta ttttatccac cgtggttct ttttgtatca      720 ttggtggaca atgatatatt tatattgttt gttcatcact cgatgtgcga tgaaatttca      780
agatcactac gactctgtga attcagttag taggtggttg atttgcctcg aaaccgtgtt      840
tatggcaaat gaccaataca tctatttaaa tgcttagaat attcattttg cgttttttt      900 gcaattccgt ttcgcccaca tatgtaggtt cgccagattt tccatgctag tggttgtcta      960
gagttagttc tcttttatta ccacttttgt accgacttta tttacggatt aattatcatc     1020
ataaacccac ataatataat gtcatagttt gattgtcatt gctcgatatg gcgcatgcac     1080
aagttgatat actatttgac gagtgtttgg ttggtacttg tacgttttgt acttgtgata     1140
tattattgtg taatagttta tgaaaatttt tatggttgac attccaacta aaaaatttac     1200
ttaatggtag agttatacaa acccaaaatc ttgatgtcgg agatcctcaa attaatgtac     1260
atatagttga atattaggtt gcaacagata caagggggtat taaatatatt gagcatatcc     1320
tcaagtggaa tcaatgtcaa atctgaaata tcgtttaatt tccctaagta gaatggatgt     1380
```

-continued

```
cctagatttt taattggtca tgtctatgta ttaagtatat attacttaaa aagtataaat    1440
taattagagc ccgttgctgc tagaaactgc aaattttaaa caaaaatagt gcttgtgaag    1500
ggttgacatt gatgaatgtt tatgattaat gaggcatata ccccattgat gctaaattga    1560
ttctttttaa ctcatgaggc atacctggct tggctgggat tgttacgtat atatatagct    1620
gagtttaatt atctgctcac agtgtgcata aacctaactc cttataccac tttacttctt    1680
tatcaacttg gtttcttgca aggag                                          1705

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
tattatatgg atccgctgga gttc                                             24

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
ctccagccat ggctgaattt gtt                                              23

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
ttattgaatt ggatcccact tgtc                                             24

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
ttaccatggt ccccaagcta gagag                                            25

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
aggtaggatc ctttatagtt ttg                                              23

<210> SEQ ID NO 9
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
gcaagaggta ggatccctat cta                                             23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
gcttgtggat ccttgacatt ggt                                             23

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
aacctcggat ccgcgtaagc at                                              22

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
ctccagccat ggctgaattt gtt                                             23

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
gcaaggatcc tgttacctat at                                              22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
actaggatcc agatttaaga aa                                              22

<210> SEQ ID NO 15
<211> LENGTH: 22
<212> TYPE: DNA
```

<213> ORGANISM: Artificial Sequence
<220> FEATURE:
<223> OTHER INFORMATION: Description of Artificial Sequence: Synthetic
      Primer

<400> SEQUENCE: 15
aggatccatc ccgaaattat gc                                          22

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
ccacaagtgg atccaatgtc aaa                                         23

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
ttaccatggt ccccaagcta gagag                                       25

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
gtgatctgca ggtgcagctt gacaaccg                                    28

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
gtggccatgg ctccttgcaa gaaaccaagt tgat                             34

<210> SEQ ID NO 20
<211> LENGTH: 975
<212> TYPE: DNA
<213> ORGANISM: Medicago truncatula

<400> SEQUENCE: 20
ccgcgtaagc atagctcagt tggcagagac atgcattatt atatgtaggg gctggggttc    60
aaaccccgga cacccacctt attcatcttg aaaaatatga attctaacca ctaaattact   120
tgaccaaaat aacccaaaat cctgatgtag gagatcctct gattaatgta taattttga    180 aagaatgtat aacatatagt tgaatattag gttgcaacag atacaagggg tattaaatat   240
attgagcata tcctcaagtg gaatcaatgt caaatctgaa atatcgttta atttccttaa   300
cggatgtcct atattttca ttggttatgt ctatgtatta agaatatatt acttaaaaac   360

```
tataaattaa ttagagtcca acttaaaatt ttattaagtt acaaaaaata gtgcttgtga      420
agcgttgaca ttggtgaatg cttatgatta attaggcata taccccattg atgctaaatt      480
gattcttttt gactttggat gcattcctga tttggctagg attgttacct atatatagct      540
gagtttgatt atctgctcac agtgtgcata aacctagctt ctcataccac tttacttctt      600
tatcaacttg gcttcttgca agaggtacga actctatcta tctcccttat tgagtttgta      660
gacaccaaat gagtattcat gttgtacatt ttttttggc aaatcttggt cgcatcatac       720
aactgtagag attaatggct cgagataact aagatatatt taaagagttt agtactcgag      780
tgtatgtgtg tataaaaata tataaatttt tcattggtat taggcacaat ttaggtaggt      840
tactttatag ttttgagcag tttatccatt tcttacctca gcctcacaaa tgtcaagtta      900
gttttttttt tgtttactaa tatttaatgt gtcttgtgct taattatgca gggaaaaact      960
aggtaacaaa ttcag                                                       975

<210> SEQ ID NO 21
<211> LENGTH: 551
<212> TYPE: DNA
<213> ORGANISM: Medicago truncatula

<400> SEQUENCE: 21
ttgacattgg tgaatgctta tgattaatta ggcatatacc ccattgatgc taaattgatt       60 cttttttgact ttggatgcat tcctgatttg gctaggattg ttacctatat atagctgagt     120
ttgattatct gctcacagtg tgcataaacc tagcttctca taccacttta cttctttatc      180
aacttggctt cttgcaagag gtacgaactc tatctatctc ccttattgag tttgtagaca      240
ccaaatgagt attcatgttg tacatttttt tttggcaaat cttggtcgca tcatacaact      300
gtagagatta atggctcgag ataactaaga tatatttaaa gagtttagta ctcgagtgta      360
tgtgtgtata aaatatata taattttcat tggtattagg caacaattag gtaggttact      420
ttatagtttt gagcagttta tccatttctt acctcagcct cacaaatgtc aagttagttt      480 ttttttgtt tactaatatt taatgtgtct tgtgcttaat tatgcaggga aaaactaggt      540
aacaaattca g                                                           551

<210> SEQ ID NO 22
<211> LENGTH: 342
<212> TYPE: DNA
<213> ORGANISM: Medicago truncatula

<400> SEQUENCE: 22
ctatctatct cccttattga gtttgtagac accaaatgag tattcatgtt gtacattttt       60
ttttggcaaa tcttggtcgc atcatacaac tgtagagatt aatggctcga gataactaag      120
atatatttaa agagtttagt actcgagtgt atgtgtgtat aaaaatatat ataattttca      180
ttggtattag gcacaattta ggtaggttac tttatagttt tgagcagttt atccatttct      240
tacctcagcc tcacaaatgt caagttagtt ttttttttgt ttactaatat ttaatgtgtc      300
ttgtgcttaa ttatgcaggg aaaaactagg taacaaattc ag                         342

<210> SEQ ID NO 23
<211> LENGTH: 133
<212> TYPE: DNA
<213> ORGANISM: Medicago truncatula

<400> SEQUENCE: 23
ctttatagtt ttgagcagtt tatccatttc ttacctcagc ctcacaaatg tcaagttagt       60
```

```
tttttttttg tttactaata tttaatgtgt cttgtgctta attatgcagg gaaaaactag    120
gtaacaaatt cag                                                      133

<210> SEQ ID NO 24
<211> LENGTH: 962
<212> TYPE: DNA
<213> ORGANISM: Medicago truncatula

<400> SEQUENCE: 24
caatgtcaaa tctaaaaaat atctcttaat taccttaagt ggaatggatg tcctagattt     60
ttaattggtt atgtatctgt attaaggata tattactcgg aaagaataaa ttagcatgtg    120
aactattata gttccctaaa aaaaaagtc aactattata gtggttttcc tctaaaaaag    180
agagtaaatt acacttcgct ttccttacag atgtttgaat tactgttcca tctcctctta    240
tattaaaata tacattttat tctcctctta ttcaaaacat attatgctaa aaaaaaaatc    300
tattagggat tttgaatcgt tgaacaacat aattgtttta cttaagtctt aaggtgttta    360
aatctcttta ggtcaacatc ccgaaattat gcttaagcat gtttaaattt gtgattaatg    420
aaattacttt ggtgattagc tagtgaattt caactcttga tatatccaat agcaattgcc    480
gcaaaagttg tataaattta gttgtacaaa tatcatttat ctataataca tttttcattc    540
ctaattttat atcaaataaa catggttgga tgcaagtgat tacatgtgt ttcctattat    600 ttatttacat tttttattac aatgatgtat gtgtttctgt taatgttgaa tgcttagggt    660
atccaagttt aatcattaat taacataact agcattcaga tttaagaaac aagaaaatta    720
attaaaaaaa aaatagtgct tataaagcgt ttacattgat gaatgcttgt gagtggtgat    780
taggttaggc ataccatt gatgctgaat tgattccttt gacctagcaa ggttcatgtt    840
acctatatat atgcatatta atagtttagc tgctcaaagt gcaggcacct agctagctcc    900
tcatacaaac ttgacttctc acaaggaggt cttctctctc tctatctctc tagcttgggg    960
ac                                                                  962

<210> SEQ ID NO 25
<211> LENGTH: 586
<212> TYPE: DNA
<213> ORGANISM: Medicago truncatula

<400> SEQUENCE: 25
catcccgaaa ttatgcttaa gcatgtttaa atttgtgatt aatgaaatta ctttggtgat     60
tagctagtga atttcaactc ttgatatatc caatagcaat tgccgcaaaa gttgtataaa    120
tttagttgta caaatatcat ttatctataa tacattttc attcctaatt ttatatcaaa    180
taaacatggt tggatgcaag tgatttacat gtgtttccta ttatttattt acatttttta    240
ttacaatgat gtatgtgttt ctgttaatgt tgaatgctta gggtatccaa gtttaatcat    300
taattaacat aactagcatt cagatttaag aaacaagaaa attaattaaa aaaaaaatag    360
tgcttataaa gcgtttacat tgatgaatgc ttgtgagtgg tgattaggtt aggcatatac    420
cattgatgct gaattgattc ctttgaccta gcaaggttca tgttacctat atatatgcat    480
attaatagtt tagctgctca aagtgcaggc acctagctag ctcctcatac aaacttgact    540
tctcacaagg aggtcttctc tctctctatc tctctagctt ggggac                   586

<210> SEQ ID NO 26
<211> LENGTH: 266
<212> TYPE: DNA
<213> ORGANISM: Medicago truncatula
```

<400> SEQUENCE: 26

```
cagatttaag aaacaagaaa attaattaaa aaaaaaatag tgcttataaa gcgtttacat      60
tgatgaatgc ttgtgagtgg tgattaggtt aggcatatac cattgatgct gaattgattc     120
ctttgaccta gcaaggttca tgttacctat atatatgcat attaatagtt tagctgctca     180
aagtgcaggc acctagctag ctcctcatac aaacttgact tctcacaagg aggtcttctc     240
tctctctatc tctctagctt ggggac                                          266
```

<210> SEQ ID NO 27
<211> LENGTH: 126
<212> TYPE: DNA
<213> ORGANISM: Medicago truncatula

<400> SEQUENCE: 27

```
tgttacctat atatatgcat attaatagtt tagctgctca aagtgcaggc acctagctag      60
ctcctcatac aaacttgact tctcacaagg aggtcttctc tctctctatc tctctagctt    120
ggggac                                                                126
```

<210> SEQ ID NO 28
<211> LENGTH: 1698
<212> TYPE: DNA
<213> ORGANISM: Medicago truncatula

<400> SEQUENCE: 28

```
ctgcaggctc aaaagggtct ttgagttttg aagaaaaatg ggtttcttc atagtttatt       60
attagcttta tgtttggttt tgaatttggt gtttgtgtgt aatggaggca gaactagtac     120
ttttgttagg aaagttgaga agaccattga atgccacttt gatagtgatg tttttgatgt     180
tccttctggt tataatgctc cccaacaggt tcatataaca caaggtgatc atgtggggaa     240
agcagtgatc gtatcgtggg tgactgagga tgaaccaggc tcgaacgcag tgcgttactg     300
gagtaagaac agcaagcaga agaggctagc taaagggaaa attgttactt atagattttt     360
caattacact tctggtttta tccatcacac tactattagg aatttagagt acaataccaa     420
atattattac gaggttggac tcgggaacac aacaaggcag ttttggttta caactcctcc     480
tgaaatcggt cctgatgtgc catacacatt tggtctaata ggggatcttg gtcagagcta     540
tgattcaaac aagacacttt ctcactacga attgaaccca acaaaaggac aaacagtgtt     600
gtttgttgga gatctctcat atgcagataa ctacccgaat catgacaatg ttaggtggga     660
tacttgggga agatttgcag aaaggagcgt tgcttatcaa ccgtggatat ggactgttgg     720
aaaccatgaa cttgatttg ctccagaaat tggagaaaca aaaccattca agccttactc     780
gcaccgatac cgtactcctt acaaagcatc gcaaagtacc tcgccctttt ggtattctat     840
caagagagct tcagctcaca tcattgtgtt ggcttcatat tcagcatatg gaaaatatac     900
accacaatac aaatggcttg aacaggagct accaaaagtt aacaggacag aaactccttg     960
gttgattgtt ctcatgcatt caccttggta taatagctac aattatcatt acatggaagg    1020
ggaatcaatg agagtaatgt atgagccatg gtttgttaag tacaaggttg atgtcgtgta    1080
tgctggccat gtccacgcct atgaacgttc tgaacgtgtg tccaatgttg catataatgt    1140
tgtaaatggt atttgcactc ctataaaaga tcaatcagct cctgtataca taaccattgg    1200
agatggaggg aaccttgaag gcttagcaac caacatgaca gaaccacaac cagagtactc    1260
agcatacaga gaggccagct ttggacatgc catttttgac ataaagaaca gaacacatgc    1320
tcactacagc tggcatagga atcaagatgg ttactctgtt gaggctgatt ctcattggtt    1380
```

```
cttcaacaga ttttggcacc cagttgatga ttccacaact catgtttccc attaacacgt   1440
tgatgttaag caataaagtc atatgattat gtaattattg tttgtgggtc aataccacca   1500
acaattatga ttatcataat cattacccttt cattttactt tgtatcactg ttatataact   1560
gcaaaggaag aagtttcatt tgtaatttgt aattttcttt ttgttgtaat aactatatag   1620
atgcagatag gaaccccaaa atgaaatcct atacctcaga cctatggctc ctaaaaaaaa   1680
aaaaaaaaaa aaaaaaa                                                  1698

<210> SEQ ID NO 29
<211> LENGTH: 1632
<212> TYPE: DNA
<213> ORGANISM: Medicago truncatula

<400> SEQUENCE: 29
atgggttctg ttttggtgca tactcatgtt gttacactgt gtatgttgtt attatcacta     60
agttcaatcc ttgttcatgg tggagttcca accacactgg atggaccttt caagcctgtg    120
acagttcctc tagacaagag cttccgtgga aacgctgtgg acataccaga cacagatcct    180
cttgttcaaa gaaatgttga agcttttcaa cctgaacaaa tctctctttc actctctacc    240
tcccatgact ctgtttggat ttcttggatt acaggagaat tccaaattgg ggagaatata    300
gaaccattag atcctgaaac agttggtagc atagttcaat atggaaggtt tggaaggtca    360
atgaatggcc aagctgttgg ttattcccctt gtgtatagtc agctatatcc ttttgaagga    420
cttcagaact atacttctgg aattatacat catgttcgtc tcacaggatt aaagcccaac    480
acactatatc aatatcaatg tggagatcct tctttgtcag caatgagtga tgttcattat    540
ttcagaacaa tgccggtttc aggtcccaag agttacccta gcagaatcgc cgtggttgga    600
gacttaggtc ttacatacaa tacgacatcc actgtcaatc atatgatcag caatcatcct    660
gatcttattc tattggttgg agatgctagt tatgctaaca tgtatcttac taatggcact    720
ggttcagatt gctactcttg ttcatttttct aatactccta tccatgaaac atatcaacca    780
cgttgggatt attggggaag gtacatggaa ccattgattt ccagtgtccc ggtaatggta    840
gtagaaggga atcatgagat agaagaacaa gctgtaaaca agacattcgt tgcttatagt    900
tctcgatttg catttccgtc ggaagagagt gggtcatctt caactttata ttattctttc    960
aatgcgggag gaatacattt tataatgctc ggttcctaca tatcatacga caaatcaggg   1020
gaccagtaca aatggttgga gaaggatttg gcttctcttg atagggaagt aactccatgg   1080
ttggtagcta catggcatgc accttggtac agcacttaca agtcacatta tagagaagcg   1140
gagtgtatga gggtcaatat ggaagattta ttatataaat atggtgttga cattgtctttt   1200 aacggacatg ttcatgccta tgagagatcg aaccgtgtat ataactacac attggatccg   1260
tgcggtcctg tttatatcac agttggtgac ggtggtaatc gggaaaagat ggcaattact   1320
catgcagatg aaccaggaaa ctgtcctgaa ccattaacta caccagataa atttatgaga   1380
ggtttctgcg ccttcaattt tacttccggt ccagcagcag gtaaattctg ttgggaccaa   1440
cagcctgatt atagtgcttt tcgcgaaagc agcttcggtc atgggattct agaggtgaag   1500
aatgaaactc atgccttatg gagttggaac cgcaatcaag actattatgg aactgctggt   1560
gatgaaattt acattgttag gcaacctgat aagtgtccac cagttatgcc agaggaggca   1620
cataatacat ga                                                       1632

<210> SEQ ID NO 30
<211> LENGTH: 8
```

```
<212> TYPE: DNA
<213> ORGANISM: Artificial Sequence
<220> FEATURE:
<221> NAME/KEY: modified_base
<222> LOCATION: (2)..(7)
<223> OTHER INFORMATION: n = a, c, g or t/u
<220> FEATURE:
<223> OTHER INFORMATION: Description of Artificial Sequence:  Synthetic
      Primer

<400> SEQUENCE: 30 gnatatnc                                                                        8

<210> SEQ ID NO 31
<211> LENGTH: 5
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 31 atatt                                                                           5
```